US006268176B1

(12) United States Patent
Gemmill et al.

(10) Patent No.: US 6,268,176 B1
(45) Date of Patent: Jul. 31, 2001

(54) TRC8, A GENE RELATED TO THE HEDGEHOG RECEPTOR, PATCHED

(75) Inventors: Robert M. Gemmill, Englewood; Harry A. Drabkin, Denver, both of CO (US)

(73) Assignee: University Technology Corporation, Boulder, CO (US)

( * ) Notice: Subject to any disclaimer, the term of this patent is extended or adjusted under 35 U.S.C. 154(b) by 0 days.

(21) Appl. No.: 09/268,140

(22) Filed: Mar. 12, 1999

Related U.S. Application Data

(60) Provisional application No. 60/077,723, filed on Mar. 12, 1998.

(51) Int. Cl.[7] .............................. C12P 21/06; C12P 19/34; C12Q 1/68; A61K 38/00; C07K 1/00

(52) U.S. Cl. ........................... 435/69.1; 435/6; 435/91.1; 530/300; 530/350

(58) Field of Search .......................... 435/6, 91.1, 91.2, 435/69.1, 183, 252.3, 320.1; 436/94; 536/23.1, 24.3, 24.33, 25.3; 530/300, 350

(56) References Cited

PUBLICATIONS

Gemmill et al., The hereditary renal cell carcinoma 3; 8 translocation fused FHIT to a patched–related gene, TRC8. Proc. Natl. Acad. Sci. USA 95, 9572–9577, Aug. 1998.*

Carstea, E. D.; Morris, J. A.; Coleman, K. G.; Loftus, S. K.; Zhang, D.; Cummings, C.; Gu, J. Rosenfeld, M.A.; Pavan, W. J.; Krizman, D. B.; Nagle, J. Polymeropoulos, M. H.; Sturley, S. L.; Ioannou, Y. A.; Higgins, M. E.; Comly, M. Cooney, A., Brown, A.; Kaneski, C. R.; Blanchette–Mackie, J.; Dwyer, N. K.; Neufeld, E. B.; Chang, T.; Liscum L. Strauss III, J. F.; Ohno K.; Zeigler, M.; Carmi, R.; Sokol, J.; Markie, D.; O'Neill, R. R.; van Diggelen, O.P.; Elleder, M.; Patterson, M. C.; Brady, R. O.; Vanier, M. T.; Pentchev, P. G. and Tagle, D. A.; Niemann–Pick C1 Disease Gene: Homology to Mediators of Cholesterol Homeostasis, Science, Jul. 11, 1997, vol. 277, pp. 228–231.

Chin, D. J.; Gil, G.; Russell, D. W.; Liscum, L.; Luskey, K.L.; Basu, S. K.; Okayama H.; Berg, P.; Goldstein, J.L.; and Brown, M. S.; Nucleotide Sequence of 3–Hydroxy–3–Methyl–Glutaryl Coenzyme A Reductase, A Glycoprotein Of Endoplasmic Reticulum, Nature, Apr. 12, 1984, vol. 308, pp. 613–617.

(List continued on next page.)

Primary Examiner—Ethan Whisenant
Assistant Examiner—Frank Lu
(74) Attorney, Agent, or Firm—Townsend and Townsend and Crew LLP

(57) ABSTRACT

The present invention provides the sequence for a novel gene called TRC8 which is located on chromosome 8. Various types of alterations in the gene have been shown to be associated with renal and thyroid tumors. One such alteration involves a 3;8 translocation which interrupts TRC8 and results in a fusion with the 3p14 gene, FHIT. Another alteration includes a mutation in the 5' untranslated region of TRC8. Thus, the invention further provides sequences corresponding to the gene fusions created during the translocation, as well as the sequence of the gene containing the mutation in the 5' region. The invention further provides methods for detecting alterations in TRC8 which have potential utility in the diagnosis of tumors.

2 Claims, 8 Drawing Sheets

OTHER PUBLICATIONS

Freemont, Paul S., The Ring Finger, *Annals of the New York Academy of Sciences*, Jun. 11, 1993, vol. 684, pp. 174–192.

Goodrich, Lisa V.; Milenkovic, Ljiljana; Higgins, Kay M. and Scott, Matthew P.; Altered Neural Cell Fates And Medulloblastoma In Mouse Patched Mutants, *Science*, Aug. 22, 1997, vol. 277, pp. 1109–1113.

Hahn, H.; Wicking, C.; Zaphiropoulos, P. G.; Gailani, M. R.; Shanley, S.; Chidambaram, A.; Vorechovsky, I.; Holmberg, E.; Unden, A. B.; Gillies, S.; Negus, K.; Smyth, I.; Pressman, C.; Leffell, D. J.; Gerrard, B.; Goldstein, A. M.; Dean, M.; Toftgard, R.; Chenevix–Trench, G.; Wainwright, B. and Bale, A. E.; Mutations Of The Human Homolog Of Drosophila Patched In The Nevoid Basal Cell Carcinoma Syndrome, *Cell*, Jun. 14, 1996, vol. 85, pp. 841–851.

Hooper, J. E. and Scott, M.P.; The Drosophila Patched Gene Encodes A Putative Membrane Protein Required For Segmental Patterning, *Cell*, Nov. 17, 1989, vol. 59, pp. 751–765.

Hua, Xianxin; Nohturfft, Axel; Goldstein, Joseph L. and Brown, Michael S.; Sterol Resistance in CHO Cells Traced To Point Mutation In SREBP Cleavage—Activating Protein, *Cell*, Nov. 1, 1996, vol. 87, pp. 415–426.

Johnson, R. L.; Rothman, A. L.; Xie, J.; Goodrich, L. V.; Bare, J. W.; Bonifas, J. M.; Quinn, A. G.; Myers, R. M.; Cox, D. R.; Epstein, Jr., E. H. and Scott, M. P.; Human Homolog Of Patched, A Candidate Gene For The Basal Cell Nevus Syndrome, *Science*, Jun. 14, 1996, vol. 272, pp. 1668–1671.

Loftus, S. K.; Morris, J. A.; Carstea, E. D.; Gu, J. Z.; Cummins, C.; Brown, A.; Ellison, J.; Ohno, K.; Rosenfeld, M. A.; Tagle, D. A.; Pentchev, P. G. and Pavan, W. J.; Murine Model of Niemann–Pick C Disease: Mutation In A Cholesterol Homeostatis Gene, *Science*, vol. 277, Jul. 11, 1997, pp. 232–235.

Luskey, K. L. and Stevens, B.; Human 3–Hydroxy–3–Methylglutaryl Coenzyme A Reductase, *Journal of Biological Chemistry*, Aug. 25, 1985, vol. 260, No. 18, pp. 10271–10277.

Marigo, Valeria; Davey, Robert A.; Zuo, Yi; Cunningham, James M. and Tabin, Clifford J.; Biochemical Evidence That Patched Is The Hedgehog Receptor, *Nature*, Nov. 14, 1996, vol. 384, pp. 176–179.

Montoyama, J.; Takabatake, T.; Takeshima, K. and Hui, C.; Ptch2, A Second Mouse Patched Gene Is Co–expressed With Sonic Hedgehog, *Nature Genetics*, Feb. 18, 1998, vol. 18, pp. 104–106.

Stone, D. M.; Hynes, M.; Armanini, M.; Swanson, T. A.; Gu, Qimin; Johnson, R. L.; Scott, M.P.; Pennica, D.; Goddard, A.; Phillips, H.; Noll, M.; Hooper, J. E.; de Sauvage, F. and Rosenthal, A.; The Tumour–Suppressor Gene Patched Encodes A Candidate Receptor For Sonic Hedgehog, *Nature*, Nov. 14, 1996, vol. 384, pp. 129–134.

Teh, B. T.; Biennow, E.; Giraud S, S.; Sahien, S.; Hii, S. I.; Brookwell, R. Brauch, H.; Nordenskjold, M.; Larsson, C. and Nicol, D.; Bilateral Multiple Renal Oncocytomas And Cysts Associated With A Constitutional Translocation (8;9) (q24.1;q34.3) and a Rare Constitutional VHL Missense Substitution, *Genes, chromosomes & Cancer*, Mar., 1998, vol. 21, No. 3 pp. 260–264.

Robert M. Gemmill, James D. West, Ferenc Boldog, Naotake Tanaka, Linda J. Robison, David J. Smith, Frederick Li, and Harry A. Drabkin, "The hereditary renal cell carcinoma 3;8 translocation fuses FHIT to a patched–related gene, TRC8," Proc. Natl. Acad. Sci. USA, Aug. 1998, vol. 95, pp. 9572–9577.

\* cited by examiner

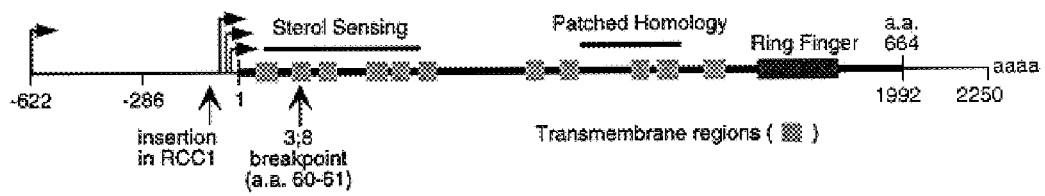

FIG. 2A

```
  1 MAAVGPPQQQ VRMAHQQIWA ALEVALRVPC LYIIDAIPNS YPDSSQSRFC
 51 IVLQIFLRLF GVFASSIVLI LSQRSLFKFY TYSSAFLLAA TSVLVNYYAS    SSD
101 LHIDFYGAYN TSAFGIELLP RKGPSLWMAL IVLQLTFGIG YVTLLQIHSI
151 YSQLIILDLL VPVIGLITEL PLHIRETLLF TSSLILTLNT VFVLAVKLKW
201 FYYSTRYVYL LVRHMYRIYG LQLLMEDTWK RIRFPDILRV FWLTRVTAQA
251 TVLMYILRMA NETDSFPISW DDFWDLICNL IISGCDSTLT VLGMSAVISS
301 VAHYLGLGIL AFIGSTEEDD RRLGFVAPVL FFILALQTGL SGLRPEERLI
351 RLSPNMCLLL TAVLHFIHGM TDPVLMSLSA SHVSSFRRHF PVLFVSACLF    PTC
401 ILPVLLSYVL WHHYALNTWL FAVTAPCVEL CLKVIVSLTV YTLFMIDGYY
451 NVLWEKLDDY VYYVRSTGSI IEFIFGVVMF GNGAYTMMFE SGSKIRAFMM
501 CLHAYFNIYL QAKNGWKTFM NRRTAVKKIN SLPEIKGSRL QEINDVCAIC
551 YHEFTTSARI TPCNHYFHAL CLRKWLYIQD TCPMCHQKVY IEDDIKDNSN
601 VSNNNGFIPP NETPEEAVRE AAAESDRELN EDDSTDCDDD VQRERNGVIQ
651 HTGAAAEEFN DDTD
```

FIG. 2B

```
HsTRC8  344  RPEERLIRLSRNMCRLLTAVLHFIEGMTDPVLMSLSASHVSSFRRHFPVLFV
DmPTC   883  QPNEYDLKIPKSLPEVYAQMPFYLHGLTDTSQIKTLIGHI....RDLSVKYE

HsTRC8  396  SACLFILVLLSYVLHHTALNTWLPRVTAFCVELCLKVIVSLTVYTL
DmPTC   931  GFGLPNYESGIPFIFHEQMNTLRSSLAMILACVLAALVLVSLLLLSV
```

FIG. 2C

```
HsTRC8    22   REVLRVPCYVKIDAIHNSYPDSEQSRFCIVEQIHDRLEGVPA.ESIVEIESQRS
HsHMG-CoA 65   STITRCIAILIY.FQEQNLRQLG.SKYILEIAGLPTIPSSSVFSTVIHPLDKE
HsPTC    289   IRVLSGYLLMLAVACLTMLRWDCSKEQGAVGLACVELVALSVBAGLGLCSEIGIS

HsTRC8    76   LFKEYEYSSAPLLAATSULVNYYPSLHIDFYEAYNTSAEGIEL...PPEKGPSLW
HsHMG-CoA 118  LTGLNEALPFPLLIIDLSRASTEKFALSSNSQDEVRENIAG...MAILGPTYT
HsPTC    344  FNAATHQVLPFLAEGVGDDVFRLAHAYSETGCNKRIPEEDRTGECRKTCASVA

HsTRC8   128  MALTVLQLTPCIEYVTLQIHSTYEQLIILDLKVPVIGLIPELHIRETEL
HsHMG-CoA 170  LDALVECLVIEVETMSGVRQPEHMCCFGCKSVLAEYFVPMTFPPACVSLVLE
HsPTC    399  LTSESNVTAPMAALIPIPAERAFSLQAAVVVVFEKAMVLLIPPAILSMDEY
```

FIG. 2D

RING-H2 MOTIF:  $Cx_2C$    $x_{9-27}$    $CxHx_2Hx_2C$    $x_{6-17}$    $Cx_2C$

TRC8 (A.A. 547-585): $C_{AI}C_{YHEFTTSARITP}C_{N}H_{YF}H_{AL}C_{LRKWLYIQDT}C_{PM}C$

FIG. 2E

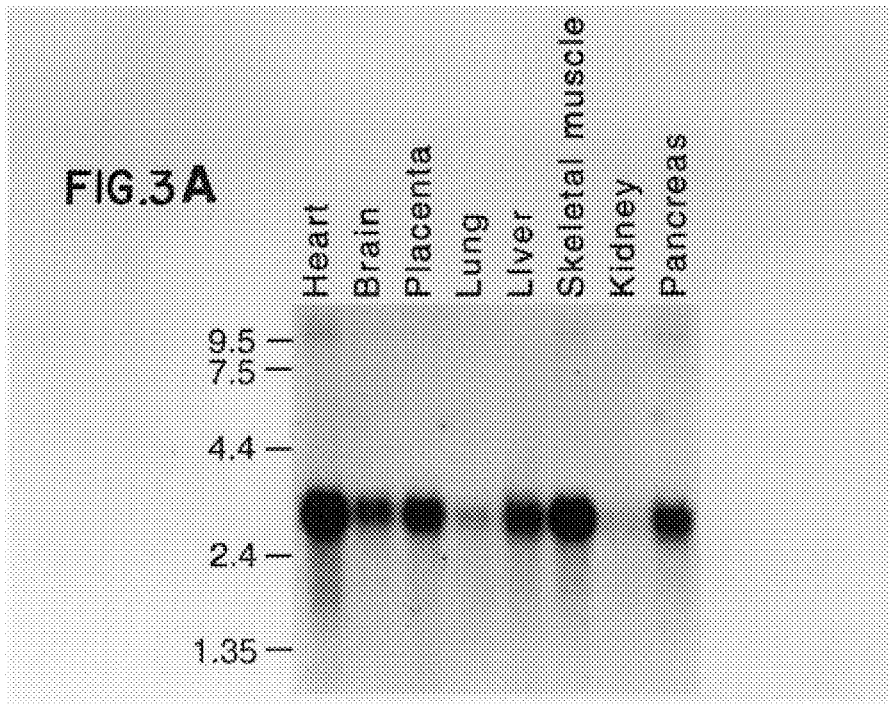
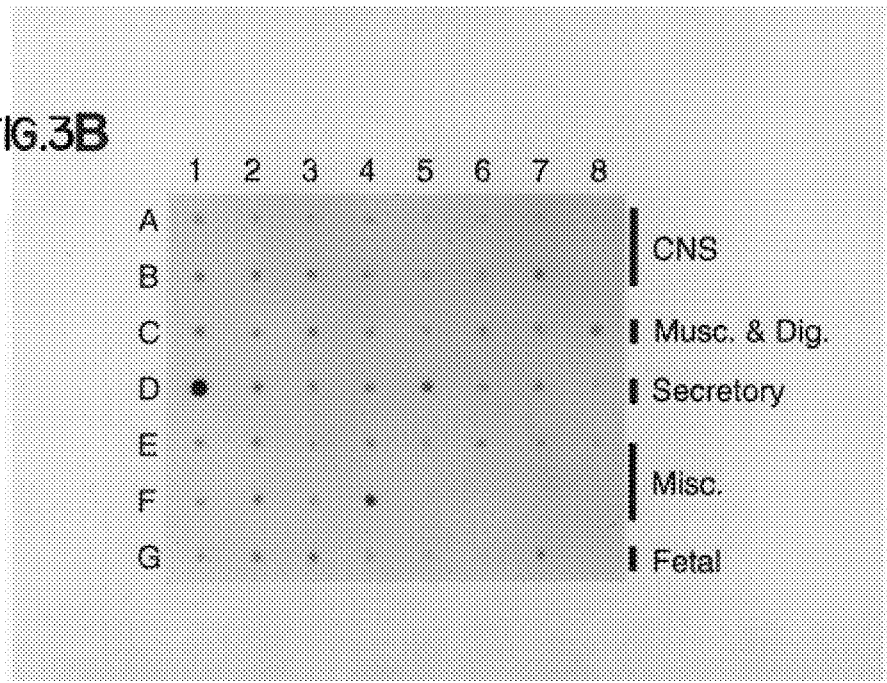

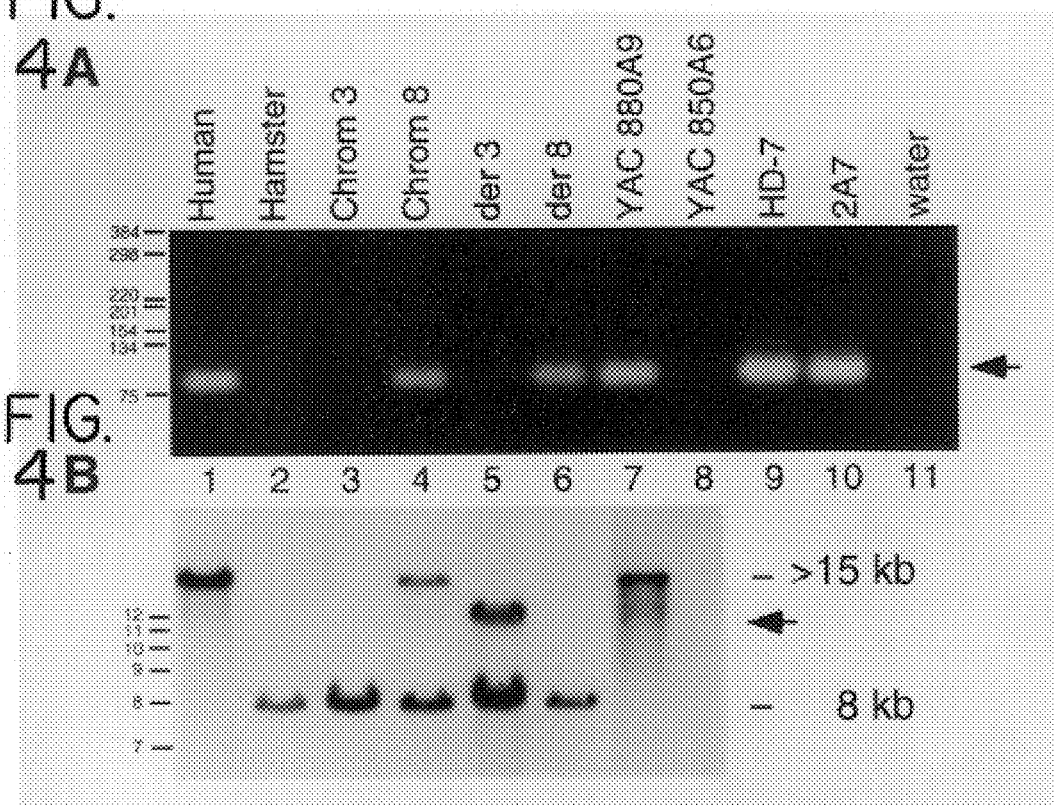

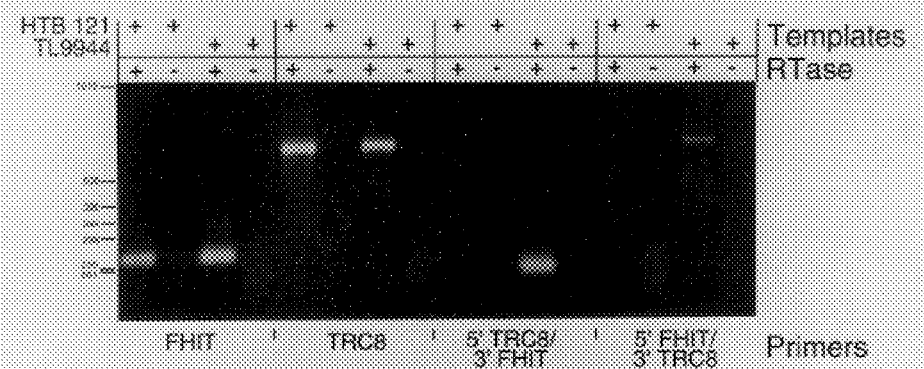
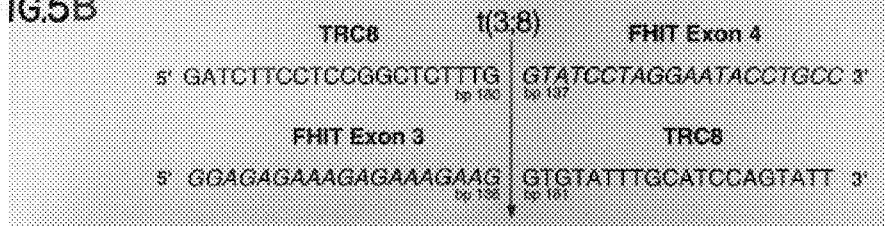

TRC8, A GENE RELATED TO THE HEDGEHOG RECEPTOR, PATCHED

RELATED APPLICATIONS

This application claims the benefit of U.S. Provisional Application No. 60/077,723, filed Mar. 12, 1998, this application being incorporated herein by reference.

STATEMENT REGARDING GOVERNMENT RIGHTS

This invention was made with support from Grant Number CA 58187 5PQ awarded by the National Institutes of Health. Therefore, the government has certain rights in this invention.

FIELD OF INVENTION

The present invention relates to alterations in a novel gene which are associated with certain renal and thyroid tumors. As such, the present invention is directed to the field of molecular genetics of tumor formation. One such alteration involves a chromosomal translocation between chromosomes 3 and 8 (typically referred to simply as t(3;8)). The 3;8 translocation results in the fusion of the novel gene TRC8 (Translocation in Renal Cancer from Chromosome 8) with a known gene named FHIT (Fragile Histidine Triad). A mutation in the 5' untranslated region has also been associated with certain renal cell carcinomas.

BACKGROUND OF THE INVENTION

The 3;8 chromosomal translocation, t(3;8)(p14.2;q24.1), was described in a family with classical features of hereditary renal cell carcinoma (RCC), i.e., autosomal dominant inheritance, early onset and bilateral disease (see A. J. Cohen, et al., *N. Engl. J. Med.* 301, 592–595 (1979)). The translocation and RCC segregated concordantly and a follow-up analysis reported the occurrence of thyroid cancer in two translocation carriers with kidney cancer (F. P. Li, et al., *Ann. Intern. Med* 118, 106–111 (1993)). Frequent 3p loss of heterozygosity (LOH) in sporadic clear-cell RCC led to the initial assumption that a critical tumor suppressor gene would be located at 3p14. Identification of the von Hippel-Lindau (VHL) gene at 3p25, frequently mutated in RCCs, provided an alternative explanation for at least some observed 3p LOH and Van den Berg et al. subsequently reported that region p21 may be a primary target for 3p LOH. (A. van den Berg and C. H. Buys, *Genes. Chromosomes. Cancer* 19, 59–76 (1997)).

Within 3p14, Ohta et al. identified a putative tumor suppressor gene (TSG), FHIT, which was interrupted in its 5' untranslated region by the 3;8 translocation (M. Ohta, et al., *Cell* 84, 587–597 (1996)). The human gene, like its yeast homologue, encodes di-adenosine (5', 5"- $P^1$, $P^3$-triphosphate) hydrolase activity. (L. D. Barnes, et al., *Biochemistry* 35, 11529–11535 (1996)). Several reports have described FHIT alterations in diverse carcinomas using nested reverse transcriptase-PCR (RT-PCR). (M. Ohta, et al., *Cell* 84, 587–597 (1996); G. Sozzi, et al., *Cell* 85, 17–26 (1996); L. Virgilio, et al., *Proc. Natl. Acad. Sci. U. S. A.* 93, 9770–9775 (1996); M. Negrini, et al., *Cancer Res.* 56, 3173 (1996); G. Sozzi, et al., *Cancer Res.* 56, 2472–2474 (1996)). Other results, however, have been contradictory.

In fact, several lines of evidence make FHIT an unlikely, or at least suspect, causative gene in the hereditary t(3;8) family. For example, the possibility that FHIT functions as a tumor suppressor is at odds with its activity as a di-adenosine hydrolase, an unprecedented tumor suppressor function (Barnes, L. D., et al., *Biochemistry* 35, 11529–11535 (1996)). The lack of substantial mutations in tumors combined with the fact that most FHIT abnormalities occur in the presence of wild-type transcripts and result from low-abundance splicing alterations, similar to those seen for TSG101, further argues against FHIT acting as a tumor suppressor (S. Thiagalingam, et al., *Cancer Res.* 56, 2936–2939 (1996); K. M. Fong, et al., *Cancer Res.* 57, 2256–2267 (1997); S. A. Gayther, et al., *Oncogene* 15, 2119–2126 (1997); F. Boldog et al., *Hum. Mol. Genet.* 6, 193–203 (1997); I. Panagopoulos, et al., *Genes. Chromosomes. Cancer* 19, 215–219 (1997); and A. van den Berg, et al., *Genes. Chromosomes. Cancer* 19, 220–227 (1997); A. Latil, et al., *Oncogene* 16, 1863 (1998)).

Moreover, there is little support for the involvement of FHIT in renal cancers (See, A. van den Berg, et al., *Genes Chromosomes Cancer* 19, 220–227 (1997); P. Bugert, et al., *Genes Chromosomes Cancer* 20, 9–15 (1997)). Similarly, the reintroduction of FHIT into tumorigenic cell lines was inconsistent in suppressing tumors, including the fact that a hydrolase "dead" mutant appeared active (Z. Siprashvili, et al., *Proc. Natl. Acad. Sci. USA* 94, 13771–13776 (1997)). Otterson et al. (*J. Natl Cancer Inst.* 90, 426–432 (1998)) introduced FHIT into six carcinoma cell lines and observed no effects on proliferation, morphology, cell-cycle kinetics, or tumorigenesis.

In earlier work, the present inventors also identified a series of 3p14 deletions, many not involving FHIT exons, which overlapped FRA3B in various carcinoma cell lines (F. Boldog, et al., *Hum. Mol. Genet.* 6, 193–203 (1997)). However, spontaneous deletions also were observed in non-tumor backgrounds. Thus, the close association of FHIT exon 5 with FRA3B suggested that its loss might be primarily related to genomic instability, in contrast to negative selection during tumor development. Although another 3p14 gene might exist, sequence data totaling 160 kb from FRA3B (F. Boldog, et al., *Hum. Mol. Genet.* 6, 193–203 (1997)) (plus GenBank updates AF023460 and AF023461), together with 135 kb of nonoverlapping sequence from Inoue et al. (*Proc. Natl. Acad. Sci. USA* 94, 14584–14589 (1997)), failed to show any additional definitive genes.

It was also noted that FHIT, in one parotid adenoma, underwent fusion with the high mobility group protein gene (HMGIC), the causative gene in a variety of benign tumors (J. M. Geurts, et al., *Cancer Res.* 57, 13–17 (1997)). That HMGIC was involved in translocations with other unrelated genes indicated that FHIT could be a bystander in the FHIT/HMGIC fusion.

Given this evidence arguing against FHIT as the causative gene in the hereditary t(3;8) family, there remained a need to identify the gene or genes involved in the 3;8 translocation that results in the formation of tumors, especially renal and thyroid cancers. Given the correspondence between the 3;8 translocation and certain tumors, identification of the gene involved in the 3;8 translocation could also have value in the diagnosis of other tumors which result from other types of alterations to the gene involved in the 3;8 translocation.

SUMMARY OF THE INVENTION

The present invention satisfies the need identified above by describing the cloning and sequencing of human DNA sequences which are rearranged in the t(3;8)(p14.2;q24.1) chromosomal translocation which occurs in renal and thyroid carcinomas. This chromosomal translocation or rearrangement was shown to fuse sequences from a novel gene which the present inventors have named TRC8 (short for Translocation in Renal Cancer from Chromosome 8) on chromosome 8q with the FHIT gene on chromosome 3p (the FHIT gene sequence is set forth as SEQ ID NO:8; the corresponding amino acid sequence is set forth as SEQ ID NO:9). The sequence of the novel TRC8 gene and the TRC8 protein, as well as the sequence of the t(3;8) fusion genes (5'TRC8/3' FHIT and 5'FHIT/3' TRC8) and the fusion proteins encoded by these fused genes are disclosed herein. A summary of certain aspects the present invention has recently been published in the scientific literature (R. M. Gemmill, et al., *Prot. Natl. Acad. Sci.* 95, 9572–9577 (1998)).

Identification of this gene is important because various types of alterations or mutations of TRC8 appear to be involved with different types of tumors and cancers. As just noted, the 3;8 translocation is involved in certain renal cancers. As described in greater detail below, a tumor-specific mutation in the 5' untranslated region is associated with certain renal carcinomas. Additionally, recent work by B. T. Teh and coworkers (Genes Chromosomes Cancer 21, 260–264 (1998)) suggests that another rearrangement involving TRC8 (a (8;9)(q 24.1;q 34.3) translocation) may be associated with certain renal oncocytomas. Thus, detection of alterations in TRC8 has utility in the detection of tumor formation.

More particularly, the present invention provides an isolated polynucleotide molecule encoding the polypeptide comprising the amino acid sequence of SEQ ID NO:2. In one particular aspect, the polynucleotide is the polynucleotide molecule of SEQ ID NO:1, or variants thereof. In another aspect, the polynucleotide comprises nucleotides 238 to 2229 of SEQ ID NO:1. The present invention further contemplates fragments of the polynucleotide comprising SEQ ID NO:1 that are at least 50 nucleotides, at least 100 nucleotides, at least 250 nucleotides, at least 500 nucleotides and at least 1000 nucleotides in length.

In another aspect, the present invention provides a polynucleotide sequence which hybridizes to the polynucleotide sequence of SEQ ID NO:1 under stringent conditions. The invention further provides polynucleotide sequences comprising the complement of SEQ ID NO:1 or variants thereof. Such complementary nucleic acid sequences may include the complement of the entire sequence of SEQ ID NO:1, or fragments thereof. More particularly, the present invention provides an isolated nucleic acid molecule comprising a nucleotide sequence selected from the group consisting of: (a) a deoxyribonucleotide sequence complementary to nucleotides 238 to 2229 of SEQ ID NO:1; (b) a ribonucleotide sequence complementary to nucleotides 238 to 2229 of SEQ ID NO:1; (c) a nucleotide sequence complementary to the deoxyribonucleotide sequence of (a) or to the ribonucleotide sequence of (b); (d) a nucleotide sequence of at least 12 consecutive nucleotides capable of hybridizing to nucleotides 238 to 2229 of SEQ ID NO:1; and (e) a nucleotide sequence capable of hybridizing to a nucleotide sequence of (d).

In a yet a further embodiment, the present invention provides an isolated polynucleotide comprising at least a portion of SEQ ID NO:1 or variants thereof which are contained in a recombinant expression vector. The recombinant vector may be contained within a host cell in another aspect of the present invention. The present invention is not limited by the particular type of host cell that can be utilized. Thus, for example, the host cell may be a human cell, a yeast cell, a bacterial cell, etc.

The present invention also provides a method for detecting the presence of TRC8 in a biological sample. The method comprises the steps of: (a) selecting a probe from SEQ ID NO:1 which specifically hybridizes to TRC8; (b) hybridizing the probe with a biological sample; (c) detecting the presence of a hybridization complex formed by the hybridization of the probe with the TRC8 nucleic acid in the sample, wherein the presence of the complex is indicative of the presence of TRC8 nucleic acid in the biological sample.

In a further embodiment, the present invention provides primers which are specific for TRC8 and which can be used in polymerase chain reaction tests to detect the gene. For example, the present invention provides polynucleotide molecules comprising a nucleotide sequence selected from the group consisting of SEQ ID NO:19 to SEQ ID NO:45, although this is not an exhaustive list of such primers.

A method for producing a polypeptide comprising the amino acid sequence of SEQ ID NO:2 or fragments thereof is also provided for by the present invention. This method generally comprises: (a) culturing a host cell which includes an expression vector containing an isolated polynucleotide encoding at least a fragment of the TRC8 polypeptide under conditions suitable for the expression of the TRC8 polypeptide and (b) recovering the polypeptide from the host cell culture. The present invention further provides a polypeptide product of the expression in a host cell of a DNA according to the method just described.

An isolated polynucleotide molecule including sequences located in the 5' flanking region to the coding region of TRC8 (SEQ ID NO:6) is also provided for by the present invention. More specifically, these sequences include nucleotides in the 5' untranslated region, exon 1 and a portion of the coding region of TRC8. The present invention also includes isolated nucleic acid molecules which are complementary to the nucleotide sequence of SEQ ID NO:6 or fragments thereof.

In another aspect, the invention includes an isolated polynucleotide molecule of SEQ ID NO:7 which occurs in certain sporadic renal cell carcinomas. More specifically, the present invention includes an isolated polynucleotide molecule comprising nucleotides 153–176 of SEQ ID NO:7. The present invention further contemplates sequences which are complementary to these sequences found in sporadic renal cell carcinomas.

In yet a further embodiment, the present invention provides isolated polynucleotides which correspond to the two gene fusions created after the t(3;8)(p14.2;q24.1) translocation event, i.e. the TRC8/FHIT fusion (SEQ ID NO:10) and the FHIT/TRC8 fusion (SEQ ID NO:11). As used herein, the TRC8/FHIT fusion or gene refers to the reciprocal fusion wherein the 5' region of TRC8 is fused to the 3' region of FHIT; the term FHIT/TRC8 fusion or gene refers to the fusion wherein the 5' region of FHIT is fused to the 3' region of TRC8 (see FIG. 1 for pictorial view of the translocation). For each of these two gene fusions, the present invention also provides an isolated polynucleotide sequence selected from the group consisting of: (a) a deoxyribonucleotide sequence complementary to the gene fusion, (b) a ribonucleotide sequence complementary to the gene fusion; and a nucleotide sequence complementary to the deoxyribonucleotide sequence of (a) or to the ribonucleotide sequence of (b).

Utilizing the sequences of the TRC8/FHIT and FHIT/TRC8 fusion genes, the present invention provides methods of identifying the presence of nucleic acids containing the TRC8/FHIT or FHIT/TRC8 fusions. In particular, the sequences described herein can be used to detect the gene fusions by means well-known in the art such as Southern and Northern blots and the like, fluorescence in situ hybridization (FISH), polymerase chain reaction (PCR) amplification and other nucleic acid hybridization and detection methods.

Because, as set forth above, various alterations of TRC8 have been shown to be associated with at least certain renal and thyroid carcinomas, the nucleotide sequences described herein can be used as a diagnostic for assessing renal or thyroid tumor formation in humans. In general, such diagnostic methods involve determining whether the TRC8 gene has been rearranged or mutated, a rearranged or mutated TRC8 gene being indicative of a renal or thyroid tumor. A variety of techniques can be utilized to determine whether the TRC8 gene has been altered as would be appreciated by those skilled in the art including PCR analysis, various amplification and hybridization methods, including for example, single-stranded conformational polymorphism (SSCP) analysis.

An example of one specific diagnostic method involves ascertaining whether there is a breakpoint in the TRC8 gene between bases 418 and 419 of the nucleotide sequence of SEQ ID NO:1. Thus, for example, nucleic acid probes which span the fusion site of the TRC8/FHIT fusion (between bases 418 and 419 of SEQ ID NO:10) or the fusion site of the FHIT/TRC8 fusion (between bases 252–253 of SEQ ID NO:11) can be used to detect a 3;8 chromosomal translocation by contacting the nucleic acid probe with a biological sample and then determining whether the probe specifically hybridizes to TRC8/FHIT DNA or to FHIT/TRC8 DNA, respectively. More specifically, a method of the present invention may include: (a) contacting one of the nucleic acid probes which span the fused site of the TRC8/FHIT gene fusion with a sample and (b) determining whether the probe specifically hybridizes with DNA containing the fused site of TRC8/FHIT but not with TRC8 DNA or FHIT DNA. Similar methods can also be used with probes specific for DNA including the FHIT/TRC8 breakpoint.

BRIEF DESCRIPTION OF DRAWINGS

FIG. 2A is a schematic of TRC8 coding domains. The coding region (bold line) containing 664 amino acids extends from bp 1 to 1992 (numbering of bases in this particular figure begins with the first base of the first codon coding for the first methionine; these bases correspond to bases 238 to 2229 of SEQ ID NO:1) and is flanked by 5' and 3' UTRs (thin lines). Promoters predicted from corresponding genomic sequences are indicated by horizontal arrows. Eleven predicted transmembrane (TM) domains (light gray) and the RING-H2 motif (Ring Finger, dark gray) are indicated along with the putative sterol sensing domain and the patched homology. The 3;8 translocation breakpoint occurs within the second transmembrane segment disrupting the sterol sensing domain (SSD) between amino acids 60 and 61 of SEQ ID NO:2. The position of a mutation found in the sporadic kidney tumor RCC #1 is indicated.

FIG. 2B shows the predicted amino acid sequence of TRC8 (SEQ ID NO:2). The sequence (also listed in GenBank as accession number 3395787) begins with the first methionine present in the isolated cDNAs. The 3:8 translocation breakpoint occurs between amino acids 60 and 61. Predicted TM segments are underlined and three potential glycosylation sites are indicated by asterisks. Two regions showing similarity to patched from *Drosophila melanogaster* are shaded, including the SSD and a region homologous to the second extracellular loop of patched (PTC). The RING-H2 motif is boxed.

FIG. 2C depicts the amino acid sequence homology between TRC8 (SEQ ID NO:2) and Drosophila patched (SEQ ID NO:3). A portion of the Dm Ptc sequence (amino acids 883–978 of SEQ ID NO:3; GenBank accession number 552099 (protein), M28999 (gene)) was aligned with a portion of the TRC8 amino acid sequence (residues 344 to 443 of SEQ ID NO:2) by gapped BLAST. Identical amino acids are indicated by white letters on black while similar amino acids (positive scores in a PAM25O matrix) are shaded. Two TRC8 TM segments within this homology region are underlined.

FIG. 2D shows the alignment of the amino acid sequence of human TRC8 (SEQ ID NO:2), human HMG-CoA reductase (SEQ ID NO:4) and human patched (SEQ ID NO:5) within the putative sterol-sensing domain (SSD). Human sequences for HMG-CoA reductase (residues 65–221 of SEQ ID NO:4; GenBank accession number 306865; Swissprot accession number P04035) and Patched (amino acids 440 to 601 of SEQ ID NO:5; GenBank accession number 1381236) were aligned with TRC8 by gapped BLAST. Identical amino acids are indicated by white letters on black, while similar amino acids (positive scores in a PAM25O matrix) are shaded; TM segments within the putative SSD of TRC8 are underlined.

FIG. 2E illustrates the ring-finger domain. A portion of TRC8 (amino acids 547 to 585 of SEQ ID NO:2) is shown compared to the RING-H2 consensus motif (SEQ ID NO:46).

FIG. 3A is an analysis of TRC8 expression by a Northern blot analysis. Gel resolved polyadenylated RNA (2 $\mu$g) from adult human tissues (Clontech Labs, Palo Alto, Calif.) was hybridized under recommended conditions with a 1.5 kb 3' TRC8 cDNA encompassing most of the TM segments and the ring finger (bp 83 to 1623, where bp 1 is the first base of the coding region; this corresponds to bp 321 to 1861 of SEQ ID NO:1). A second, largely non-overlapping probe (bp 1446 to 2212, where bp 1 is the first base of the coding region; this corresponds to bp 1684 to 2450 of SEQ ID NO:1) yielded essentially the same pattern. The filter was exposed for 18 hours at −80° C.

FIG. 3B is an analysis of TRC8 expression by a dot blot analysis. A Clontech human RNA master dot blot was hybridized with the same probe as in (3A) under recommended conditions and exposed for 15 h. Final wash conditions were 0.1×SSC, 0.5% SDS @ 55 ° C. for 20 min. Signals were collected on a Molecular Dynamics Phosphorimager. Blank positions included B8, F5–F8 and G8. Central nervous system tissues (A1–A8 and B1–B7) included (in order) whole brain, amygdala, caudate nucleus, cerebellum, cerebral cortex, frontal lobe, hippocampus, medulla oblongata, occipital lobe, putamen, substantia nigra, temporal lobe, thalamus, sub-thalamic nucleus and spinal cord. Musculature and digestive tissues (C1–C8) included heart, aorta, skeletal muscle, colon, bladder, uterus, prostate and stomach. Secretory tissues (D1–D8) included testis, ovary, pancreas, pituitary, adrenal, thyroid, salivary and mammary glands. Miscellaneous tissues (E1–E8 and F1–F4) included kidney, liver, small intestine, spleen, thymus, peripheral leukocytes, lymph node, bone marrow, appendix, lung, trachea and placenta. Fetal tissues (G1–G7) included brain, heart, kidney, liver, spleen, thymus and lung. All control spots (yeast and E. coli RNAs, human Cot1 and total human DNAs) were blank (not shown).

FIG. 4A illustrates the localization of 5' TRC8 sequences to chromosome 8q. Primers R-M (SEQ ID NO:19) and F-O (SEQ ID NO:20) (see FIG. 1 for general location of TRC8 to which primers hybridize) amplify an 82 bp fragment specific for the 5' portion of TRC8. Templates in lanes 1 through 11 included, respectively, AG4103 (normal human), CHO glyA⁻ (hamster), UCTP-2A3 (chromosome 3 only hybrid), 706-B6, clone 17 (chromosome 8 only hybrid), TL12-8 [t(3;8) der(3) hybrid], 3;8/4-1 [t(3;8) der(8) hybrid], YAC 880A9 (chromosome 8-specific YAC spanning 3;8 breakpoint), YAC 850A6 (chromosome 3-specific YAC spanning 3;8 breakpoint), HD-7 (genomic phage clone carrying the 3;8 breakpoint region from chromosome 8), 2A7 (longest 5' RACE clone), water control. Molecular size standards are indicated in base pairs.

FIG. 4B is a Southern blot in which the same hybrid and YAC DNAs listed in FIG. 4A were digested with EcoRI and then Southern blotted. The filter was hybridized with a 1.4 kb TRC8 cDNA fragment which derives from the 3' end. The normal human TRC8 fragment is >15 kb which is reduced to ~12 kb by the translocation (arrow). The cross-hybridizing fragment in hamster DNA (lanes 2–6) is 8 kb.

FIG. 5A shows an RT-PCR analysis of fusion product expression. RNAs isolated from the t(3;8) lymphoblastoid cell line TL9944 (R. M. Gemmill, et al., Genomics 4, 28 (1989)) and from a control breast carcinoma cell line HTB 121 were treated with or without reverse transcriptase, as indicated (+ or –) and analyzed for expression of FHIT and TRC8 by PCR. Four primers specific for 5' and 3' portions of each gene, F1 (SEQ ID NO:18) and R1 (SEQ ID NO:11) for FHIT and R-M (SEQ ID NO:19) and EMR (SEQ ID NO:21) for TRC8 (see FIG. 1 for general section of gene to which primers hybridize), were used in combination to detect both wild-type and putative chimeric transcripts. The FHIT primer pair generated a product of the expected size (231 bp), as did the TRC8 primer pair (651 bp). Reciprocal chimeric products were amplified using R-M (SEQ ID NO:19) plus R1 (SEQ ID NO:12) for 5' TRC8/3' FHIT, and F1 (SEQ ID NO:18) plus EMR (SEQ ID NO:21) for 5' FHIT/3' TRC8. Predicted sizes of the chimeric products are 188 and 694 bp, respectively. Lanes 1–16 are in order from left to right.

FIG. 5B lists the sequences of 3;8 chimeric transcripts. The RT-PCR amplified cDNAs in lanes 11 and 15, corresponding to the reciprocal chimeric transcripts, were purified and sequenced on both strands. Bases surrounding the boundary between FHIT exons 3 and 4 are shown with FHIT sequences italicized (bases 399 to 438 of SEQ ID NO:10 (5'TRC8/FHIT3' fusion) and bases 234 to 272 of SEQ ID NO:11 (5'FHIT/TRC83' fusion). The precise position of the fusion on both TRC8 and FHIT transcripts is indicated. (For TRC8, the base numbering in FIG. 5B assumes that the first base in the coding region is base number 1. Thus, bp 180 of TRC8 is bp 418 of SEQ ID NO:1. For FHIT, bp 137 corresponds to bp 253 of SEQ ID NO:8.)

DETAILED DESCRIPTION OF PREFERRED EMBODIMENTS

Figure 1:
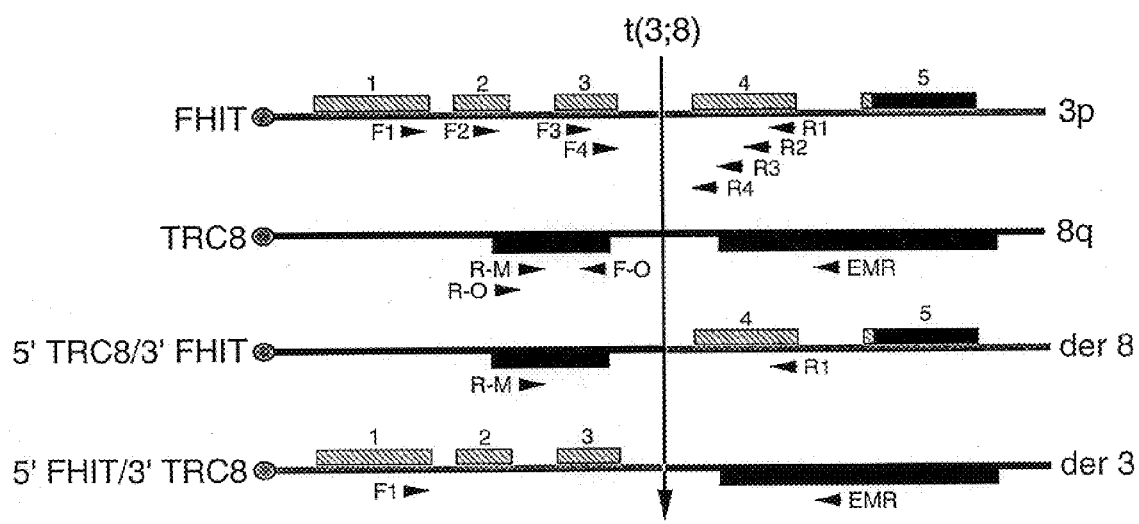
FIG. 1 illustrates a fusion of FHIT and TRC8 genes by the 3;8 translocation. Normal chromosomes 3p and 8q are shown schematically along with FHIT exons 1 through 5 (non-coding regions are shaded; coding regions are black) and TRC8 exons 1 and 2. Both genes are transcribed away from their respective centromeres (dot on left). The 3;8 breakpoint (indicated schematically by the vertical arrow) interrupts FHIT between untranslated exons 3 and 4 to generate the der (8) and der (3) chromosomes. TRC8 is interrupted between the 5' and 3' coding exons. Nested primers R1 (SEQ ID NO:12), R2 (SEQ ID NO:13) and R3 (SEQ ID NO:15) within FHIT exon 4 were used for 5' RACE (arrow heads). FHIT exon 4 oligonucleotide R4 (SEQ ID NO:17) identified bona fide RACE products which were tested with the exon 3 oligonucleotide F4 (SEQ ID NO:16) to identify putative gene fusions. The other primers indicated were used for RT-PCR and mapping experiments (F1—SEQ ID NO:18; R-M—SEQ ID NO:19; F-O—SEQ ID NO:20; and EMR—SEQ ID NO:21).

The present invention is based upon the identification and characterization of several new nucleic acid sequences: (a) the novel gene TRC8, which encodes a novel TRC8 protein, (b) a sequence including bases in the 5' flanking region to the TRC8 coding region plus exon 1, (c) a nucleotide sequence for a mutated TRC8 which was found in a sporadic renal cell carcinoma, (d) the 5' TRC8/3° FHIT fusion and the related 5' FHIT/3' TRC8 fusion, which result from a chromosomal translocation event (specifically the t(3;8)(p14.2;q24.1)), this chromosomal translocation being associated with human renal and thyroid tumors in the 3;8 family.

TRC8 appears to be a critical gene in the 3;8 translocation and appears to be linked with various tumors and cancers based on the following: (i) its similarity to patched, which in turn is responsible for the hereditary basal cell carcinoma syndrome (H. Hahan, et al., *Cell* 85, 841–851 (1996); R. L. Johnson, et al., *Science* 272, 1668–1671 (1996)), (ii) the preservation and expression of FHIT coding sequences in 3;8 translocation containing cells (in contrast to the disruption of TRC8 coding sequences), and (iii) its demonstrated mutation in a sporadic renal carcinoma. Furthermore, recent work by other researchers has provided cytogenetic evidence for another set of renal tumors that appear to be associated with alterations in TRC8, including a 8q24.1 breakpoint as in the 3;8 translocation described herein. More specifically, analysis of the lymphocytes of a patient suffering from bilateral multifocal renal oncocytomas and cysts showed a constitutional reciprocal t (8;9) (q24.1; q 34.3) Teh, et al. (*Genes Chromosomes Cancer* 21, 260–264 (1998)). The fact that several different alterations of TRC8 is associated with various tumors and cancers indicates that the detection of alterations in TRC8 has utility in the diagnosis of certain tumors and cancers. The type of alterations could include translocations such as the t(3;8), as well as substitutions, deletions, insertions, inversions, etc.

One embodiment of the present invention provides an isolated nucleic acid sequence, TRC8 (SEQ ID NO:1), which encodes the TRC8 protein (SEQ ID NO:2). As described in further detail below, TRC8 encodes a predicted 664-aa, multitransmembrane protein with similarity to patched from *Drosophila melanogaster*. This similarity includes the second extracellular domain of patched, which is involved in binding sonic hedgehog, as well as its putative sterol-sensing domain (SSD). In addition, the first 480 amino acids of TRC8 and amino acids 440–1100 of patched share an organization similarity. This similarity begins with the common SSD, followed by the divergent region that is nonconserved among patched homologues (J. Motoyama, et al., *Nat. Genet.* 18, 104–106 (1998)), and finally by the conserved second extracellular loop. TRC8 lacks the first extracellular loop of patched and likewise shows no similarity after the second extracellular loop. Therefore, although TRC8 has similarity to patched and is predicted to be a plasma membrane protein by PSORT (K. Nakai, and M. Kanehisa, *Genomics* 14, 897–911 (1992)), it is not the type of direct homologue as is the Patched 2 gene, for instance (J. Motoyama, et al., *Nat. Genet.* 18, 104–106 (1998)).

As those skilled in the art will appreciate, a number of different nucleotide sequences can encode for the TRC8 protein because of the degeneracy of the genetic code. Consequently, the present invention contemplates each and every possible variation of the nucleotide sequence that can be made by selecting from the possible codon choices for a given amino acid in the TRC8 protein sequence. One such sequence is the sequence listed as SEQ ID NO:1. More particularly, the present invention includes an isolated polynucleotide comprising nucleotides 238 to 2229 of SEQ ID NO:1 (the coding region of the TRC8 gene; the stop codon includes bases 2230 to 2232 of SEQ ID NO:1). The present invention also includes the production by synthetic chemistry of DNA sequences, or fragments thereof, which encode for the TRC8 protein and the subsequent insertion of such synthetic sequences into any of the number of currently available expression vectors and cell systems which are known to those skilled in the art.

In another embodiment, the present invention provides an isolated nucleic acid molecule comprising a nucleotide sequence selected from the group consisting of: (a) a deoxyribonucleotide sequence complementary to nucleotides 238 to 2229 of SEQ ID NO:1; (b) a ribonucleotide sequence complementary to nucleotides 238 to 2229 of SEQ ID NO:1; (c) a nucleotide sequence complementary to the deoxyribonucleotide sequence of (a) or to the ribonucleotide sequence of (b); (d) a nucleotide sequence of at least 12 consecutive nucleotides capable of hybridizing to nucleotides 238 to 2229 of SEQ ID NO:1; and (e) a nucleotide sequence capable of hybridizing to a nucleotide sequence of (d).

By inserting the TRC8 nucleic acid sequence (i.e., SEQ ID NO:1) into an appropriate vector, it is possible to prepare large quantities of the TRC8 sequence using methods which are well-known to those with skill in the art. Alternatively, the TRC8 nucleic acid sequence can be inserted into an expression vector and the vector placed in a host cell to produce the TRC8 protein (i.e. SEQ ID NO:2). The TRC8 protein can then be isolated from the host cell culture according to standard purification techniques. A number of host/vector systems are available for the amplification of the TRC8 nucleic acid sequence and/or the protein expressed by the TRC8 gene. Such systems include, but are not limited to, plasmid and viral vectors, and eukaryotic and procaryotic hosts.

The present invention also provides methods for detecting the presence of TRC8 in a biological sample. One method comprises the steps of: (a) selecting a probe from SEQ ID NO:1 which specifically hybridizes to TRC8; (b) hybridizing the probe with a biological sample; and (c) detecting the presence of a hybridization complex formed by the hybridization of the probe with the TRC8 nucleic acid in the sample, wherein the presence of the complex is indicative of the presence of TRC8 nucleic acid in the biological sample. Another method includes contacting a nucleic acid probe which is at least 12 continuous nucleotides in length and is specific for binding to human TRC8 gene with the biological sample under conditions which allow the nucleic acid probe to anneal to complementary sequences in the sample and then detecting duplex formation between the nucleic acid probe and the complementary sequences. The nucleic acid probe used may be a subsequence of the entire human TRC8 gene.

In a further embodiment, the present invention provides primers which are specific for TRC8. These primers can be used to amplify TRC8 and thus detect its presence according to PCR methodologies which are well-known in the art. In particular, the present invention provides polynucleotide molecules comprising a nucleotide sequence selected from the group consisting of SEQ ID NO:19 to SEQ ID NO:45, inclusively.

A method for producing a polypeptide comprising the amino acid sequence of SEQ ID NO:2 or fragments thereof is also provided for by the present invention. This method generally comprises: (a) culturing a host cell which includes an expression vector containing an isolated polynucleotide encoding at least a fragment of the TRC8 polypeptide under conditions suitable for the expression of the TRC8 polypeptide and (b) recovering the polypeptide from the host cell culture. The present invention further provides a polypeptide product in a host cell of a DNA according to the method just described.

An isolated polynucleotide molecule including sequences located in the 5' flanking region to the coding region of TRC8 (SEQ ID NO:6) is also provided for by the present invention. More specifically, these sequences include exon 1 and a portion of the coding region of TRC8. The present invention also includes isolated nucleic acid molecules selected from the group consisting of: (a) a deoxyribonucleotide sequence complementary to SEQ ID NO:6; (b) a ribonucleotide sequence complementary to SEQ ID NO:6;

(c) a nucleotide sequence complementary to the deoxyribonucleotide sequence of (a) or to the ribonucleotide sequence of (b); (d) a nucleotide sequence of at least 12 consecutive nucleotides capable of hybridizing to nucleotides of SEQ ID NO:6; and (e) a nucleotide sequence capable of hybridizing to a nucleotide sequence of (d).

In another aspect, the invention includes an isolated polynucleotide molecule of SEQ ID NO:7 which occurs in certain sporadic renal cell carcinomas. More specifically, the present invention includes an isolated polynucleotide molecule comprising nucleotides 153–176 of SEQ ID NO:7. In this regard, the present invention further provides an isolated nucleic acid molecule selected from the group consisting of: (a) a deoxyribonucleotide sequence complementary to nucleotides 153–176 of SEQ ID NO:7; (b) a ribonucleotide sequence complementary to nucleotides 153–176 of SEQ ID NO:7; and (c) a nucleotide sequence complementary to the deoxyribonucleotide sequence of (a) or to the ribonucleotide sequence of (b).

In another aspect, the present invention provides isolated polynucleotide sequences which correspond to the two gene fusions created after the t(3;8)(p14.2;q24.1) translocation event, i.e. the TRC8/FHIT fusion (SEQ ID NO:10) and the FHIT/TRC8 fusion (SEQ ID NO:11). As noted above, the TRC8/FHIT fusion refers to the fusion wherein the 5' region of TRC8 is fused to the 3' region of FHIT; the term FHIT/TRC8 fusion refers to the fusion wherein the 5' region of FHIT is fused to the 3' region of TRC8. For each of these two gene fusions, the present invention also provides an isolated polynucleotide sequence selected from the group consisting of: (a) a deoxyribonucleotide sequence complementary to the gene fusion, (b) a ribonucleotide sequence complementary to the gene fusion; and (c) a nucleotide sequence complementary to the deoxyribonucleotide sequence of (a) or to the ribonucleotide sequence of (b).

The present invention provides nucleic acid probes selected from the group consisting of: (a) a deoxyribonucleotide sequence which is a DNA fragment comprising contiguous nucleotides on the 5' and 3' sides of the fused site of either TRC8/FHIT fused DNA or FHIT/TRC8 fused DNA, (b) a ribonucleotide sequence complementary to the deoxyribonucleotide sequence of (a), and a nucleotide sequence complementary to the deoxyribonucleotide sequence of (a) or to the ribonucleotide sequence of (b), wherein the fused site is between bases 418 and 419 of the nucleotide sequence of SEQ ID NO:10 for the TRC8/FHIT fusion and between bases 252 and 253 of SEQ ID NO:11 for the FHIT/TRC8 fusion.

In another embodiment, the present invention provides a pair of oligonucleotides which can be used in PCR analysis for example, wherein one of the oligonucleotides specifically hybridizes with the TRC8-FHIT fused DNA comprising the contiguous nucleotide sequence of SEQ ID NO:10 on the 3' side of the fused site and the other oligonucleotide specifically hybridizes with the TRC8-FHIT fused DNA on the 5' side of the fused site, the fused site being located between bases 418 and 419 of SEQ ID NO:10. Similarly, the present invention also provides a pair of oligonucleotides wherein one of the oligonucleotides specifically hybridizes with the FHIT/TRC8 fused DNA comprising the contiguous nucleotide sequence of SEQ ID NO:11 on the 3' side of a fused site and the other oligonucleotide specifically hybridizes with the FHIT/TRC8 fused DNA on the 5' side of said fused site, said fused site being located between bases 252 and 253 of SEQ ID NO:11.

Because alterations of the TRC8 gene have been implicated with several different renal and thyroid carcinomas, the nucleotide sequences described herein can be used as a diagnostic for assessing renal or thyroid tumor formation in humans. In general, such diagnostic methods involve determining whether the TRC8 gene has been rearranged or mutated, a rearranged or mutated TRC8 gene being indicative of a renal or thyroid tumor. The mutations may be of various types including, for example, deletions, substitutions and inversions Various methods which are well known to those skilled in the art can be used to identify alterations in TRC8. One method, for example, involves using paired primer sets to amplify DNA samples. Alterations such as mutations can then be identified using single-stranded conformational polymorphism analysis (SSCP). Examples of the types of primers which could be utilized and additional specifics regarding the SSCP methodology is set forth more fully in Example 5 below.

Although the 3;8 translocation is but one of what appears to be several alterations to TRC8 which is associated with different tumors and cancers, the following methods illustrate how the 3;8 translocation can be detected. It is important to recognize, however, that similar methods could be used to detect other changes to TRC8.

One example of an assay method which can be utilized to detect the 3;8 translocation and the formation of the TRC8/FHIT and FHIT/TRC8 fusions involves selective amplification of sequences within a sample which contains the TRC8/FHIT and FHIT/TRC8 polynucleotides (SEQ ID NO:10 and SEQ ID NO:11, respectively). The present invention also includes methods which identify nucleic acids containing the TRC8/FHIT and FHIT/TRC8 fusions but which do not require sequence amplification for detection. Such methods include Southern and Northern blot hybridization tests and fluorescence in situ hybridization (FISH) of chromosomal material, using probes derived from the nucleic acids of the present invention.

As noted above, the nucleic acid probes of the present invention can be DNA or RNA probes. Such probes can be prepared according to methods which are known in the art (see for example, *Molecular Cloning*, (Sambrook, et al., Eds.), Cold Spring Harbor Press, Cold Spring Harbor, N.Y. (1989)). One with skill in the art can employ the techniques such as described in the preceding reference and the sequences described herein, or fragments thereof, as probes.

The detection methods of the present invention can be utilized with a variety of sample types. A non-exhaustive list of the type of samples that can be used include cells or tissues, extracts of cells or tissues containing protein, membranes, nucleic acids or combinations thereof, and biological fluids such as blood, serum and plasma. Methods for preparing such extracts are known in the art and can readily be adapted by one skilled in the art to obtain a sample which is appropriate for the type of detection test being conducted (see, for example, K. Budelier et al., Chapter 2, "Preparation and Analysis of DNA," M. E. Greenberg, et al., Chapter 4, "Preparation and Analysis of RNA," and M. Moos, et al., Chapter 10, "Analysis of Proteins," in *Current Protocols in Molecular Biology*, Wiley Press, Boston, Mass. (1993)).

More specifically, one diagnostic method involves ascertaining whether there is a breakpoint in the TRC8 gene between bases 418 and 419 of the nucleotide sequence of SEQ ID NO:1. For example, the nucleic acid probes described above which span the fused site of the TRC8/FHIT fusion or the FHIT/TRC8 fusion can be used to detect a 3;8 chromosomal translocation by contacting the nucleic acid probe with a biological sample and then determining whether the probe specifically hybridizes to TRC8/FHIT DNA or to FHIT/TRC8 DNA. Of course probes could also be used to probe for complementary DNA or RNA sequences to the two fused sequences. Thus, for example, a method of the present invention may include: (a) contacting one of the nucleic acid probes which span the breakpoint of the TRC8/FHIT gene fusion with a sample and (b) determining whether the probe specifically hybridizes with DNA containing the fused site of TRC8/FHIT but not with TRC8 DNA or FHIT DNA. Similar methods can also be used with probes specific for DNA including the FHIT/TRC8 breakpoint. A second method would directly detect mutations in TRC8.

The following specific examples further describe the present invention and further illustrate the features and advantages provided by the present invention.

EXAMPLE 1

Identification and Sequence Analysis of TRC8

(a) Cell Lines and Genomic Clones

Tumor cell lines were obtained from American Type Culture Collection (Gaithersburg, Md.), except for somatic cell hybrids which were generated by the present inventors previously and reported by H. A. Drabkin, et al. (*Cancer Cells* 7, 63 (1989)). The hybrids TL12-8 and 3;8/4-1 contain the der (3) and der (8) chromosomes, respectively, from the t(3;8) lymphoblastoid cell line TL9944 (without either a normal 3 or 8 chromosome). The human lymphoblastoid line AG4103 served as a normal control. Isolation of DNA and RNA was performed using standard methods.

The HD-7 genomic phage clone carrying the 3;8 translocation breakpoint from the der(8) chromosome was isolated from a library prepared from the TL9944 cell line in λ FHXII (Stratagene, Inc., La Jolla, Calif.). A chromosome 3 probe (λ4040) which maps just distal to the 3;8 breakpoint was used for screening (F. L. Boldog, et al., *Proc. Natl. Acad. Sci. USA* 90, 8509 (1993)).

(b) 5' Race

RNA was isolated from TL9944 lymphoblastoid cells carrying the 3;8 translocation (see, R. M. Gemmill, et al., *Genomics*. 4, 28 (1989)), and then subjected to RACE (see, M. A. Frohman, *PCR. Methods Appl.* 4, S40 (1994)). 5' RACE was performed essentially as described by M. A. Frohman (*Methods. Enzymol.* 218, 340 (1993)). First strand cDNA synthesis used FHIT exon 4-specific primer R1 (5'-TCAGAAGACTGCTACCTCTTCG-3'—SEQ ID NO:12) followed by dCTP tailing with terminal deoxynucleotidyl transferase. Primary amplification utilized the AAP 5'-RACE primer from a 5' RACE Kit sold by Gibco-BRL/Life Technologies, together with R2, a nested FHIT exon 4-specific primer (5'-TCAGTGGCAGGATGCACAG-3'— SEQ ID NO:13). Second round nested PCR utilized primer AUAP (also from the 5' RACE Kit sold by Gibco-BRL/Life Technologies) with R3, a second nested FHIT exon 4—specific primer (5'-GGTCTAAGCAGGCAGGTATTC-3'—SEQ ID NO:15). Products were cloned into a T-vector (pBluescript II K/S), analyzed by hybridization with additional internal FHIT oligonucleotides F4 (5'-TGGAAGGGAGAGAAAGAG-3'—SEQ ID NO:16) and R4 (5'-GGTATTCCTAGGATAC-3'—SEQ ID NO:17) and sequenced.

Because the t(3;8) breakpoint interrupts FHIT between exons 3 and 4, 5'-RACE products were generated using nested primers within FHIT exon 4 as shown in FIG. 1. Cloned amplification products were identified by hybridization with oligonucleotide R4 (SEQ ID NO:17). Nearly 80% of R4 positive clones were negative for an exon 3 oligonucleotide (F4) suggesting they might represent a gene fusion. Nine of 12 sequenced clones contained an identical novel sequence spliced exactly to the 5' end of FHIT exon 4. Mapping studies confirmed that the new sequences were derived from chromosome 8 (see below). As noted earlier, the present inventors refer to this gene as TRC8 for Translocation in Renal Cancer from chromosome 8.

(c) DNA Sequence Analysis

The coding region of TRC8 was determined from multiple cDNA clones and PCR products isolated from a human fetal brain library (Stratagene, Inc.) as well as IMAGE clone 331H8 identified from dbEST. Sequencing was performed on an AB1377 through the Colorado Cancer Center DNA Sequencing Core. Analysis for transmembrane segments was performed using five prediction programs, including PHD_htm at EMBL (http://www.emblheidelberg.de/predictprotein/), TMpred at ISREC (http://ulrec3.unil.ch/software/TMPRED_form.html), SOSUI at Tokyo University (http://www.tuat.ac.jp/~mitaku/adv_sosui/), DAS at Stockholm University (http://www.biokemi.su.se/~server/DAS/), and PSORT at Osaka University (http://psort.nibb.acjp/). All ten transmembrane segments that are underlined in FIG. 2B were predicted by at least four out of the five programs, although in most cases the programs did not agree on the precise boundaries of the segment.

The DNA sequence (SEQ ID NO:1; Genbank AF064801) contains a predicted 1992 bp open reading frame (bases 238 to 2229 of SEQ ID NO:1, or bases 1 to 1992 if the first base in the coding region is considered the first base) as shown in FIG. 2A. Upstream cDNA as well as corresponding genomic sequences are GC-rich indicative of a CpG-island. Using a promoter prediction program (http://www-hgc.lbl.gov/projects/promoter.html), four transcriptional start sites are located at −622, −55, −36 and −22 bp of the first methionine (the numbering in this instance assumes that the first bp of the coding region is base number 1; this corresponds to bp 238 of SEQ ID NO:1). The −22 site corresponded precisely to two of the nine sequenced RACE products. Use of the −622 site is suggested by the longest presently available cDNA which extends to position −286 and RT-PCR experiments have confirmed transcription to at least position −547.

The ORF is predicted to encode a 664 amino acid protein (SEQ ID NO:2) of 76 kDa (see FIGS. 2A and 2B) with at least ten membrane spanning segments. TRC8 contains two regions of similarity with the gene patched from Drosophila (the amino and sequence encoded by patched is listed as SEQ ID NO:3), the receptor for Sonic Hedgehog (SHH) (V. Marigo, et al., *Nature* 384, 176 (1996); and D. M. Stone, et al., *Nature* 384, 129 (1996)). The region from amino acids 344 to 443 of TRC8 (SEQ ID NO:2) shows the strongest match with 60% similarity and 23% identity to amino acids 883–979 of patched (residues 883 to 979 of SEQ ID NO:3) (See FIG. 2C); this region of patched represents most of the second predicted extracellular domain involved in the binding of SHH. A second region of patched similarity involves amino acids 22 to 179 of SEQ ID NO:2 and encodes a putative sterol sensing domain (SSD). Such domains, identified in HMG-CoA reductase and the sterol regulatory element binding protein (SREBP) cleavage activating protein (SCAP), consist of five membrane spanning segments arranged with a specific spacing pattern (X. Hua, et al., *Cell* 87, 415 (1996)). Patched contains a putative SSD, of unknown function, from amino acids 440 to 601 of SEQ ID NO:3 (E. D. Carstea, et al., *Sci.* 277, 228 (1997)). This region is 53% similar/17% identical to the SSD of HMG-CoA reductase (amino acids 65 to 221 of SEQ ID NO:4), as reported by D. J. Chin, et al. (*Nature* 308, 613 (1984)); the corresponding region from TRC8 (amino acids 22 to 179 of SEQ ID No:2) shows 63% similarity/17% identity (See FIG. 2D). Not wishing to be bound by any particular theory, the present inventors surmise, based upon the multiple transmembrane segments and regions of patched similarity, that TRC8 encodes a membrane bound receptor.

In addition, a perfect match with a ring-finger motif of the RING-H2 sub-type (SEQ ID NO:46) (P. S. Freemont, *Ann. N. Y A cad. Sci.* 684, 174 (1993)) was found in TRC8 between amino acids 547 to 585 of SEQ ID NO:2 as shown in FIG. 2E. The RING-H2 motif in TRC8 differs from the standard RING-finger by replacement of the fourth cysteine with a histidine. Functionally, RING-H2 motifs have been suggested to be protein-protein or protein-lipid interaction domains. That TRC8 is highly conserved, at least among mammals, is evident from two murine ESTs (dbEST clones mu78h12 and v143c01) found to be 93% and 89% identical at the nucleotide level over 971 bp.

EXAMPLE 2

Expression of TRC8

Hybridization of TRC8 to a Northern blot (CLONETECH) prepared from adult human tissues and placenta identified a message of approximately 3.0 kb (FIG. 3A). Although the longest cDNA clones total 2.5 kb, use of the −622 promoter (numbered as though the first base of the coding region is bp 1, i.e., base 238 of SEQ ID NO:1), as discussed above, would result in a 2.9-kb message, close to the observed size. Although expression in the lung and kidney appeared reduced, hybridization with a control glyceraldehyde-3-phosphate dehydrogenase probe (data not shown) indicated that there was less RNA present in these samples. A human RNA dot blot revealed TRC8 message in all tissues examined (as shown in FIG. 3B), with the highest levels in testis (D1) and placenta (F4) and adrenal (D5); the lowest level was in thymus (G6). TRC8 is expressed in both fetal (G3) and adult kidney (E1) and in adult thyroid (D6), the suspected target organs for TRC8 aberrations in the 3;8 translocation family.

EXAMPLE 3

Mapping of TRC8

TRC8 sequences were localized to the immediate region of the breakpoint on chromosome 8 by both PCR and Southern blot analysis of hybrids, "YACs" (yeast artificial chromosomes) and phage clones (See FIG. 4). PCR mapping used TRC8 specific primers R-M (5'-GCCCTGCCTTTACATCATCGAC-3'—SEQ ID NO:19) and F-O (5'-AGATCTGGAGCACGATGCAGAAC-3'—SEQ ID NO:20) which lie within a GC rich segment. PCR reactions were performed under touch-down annealing conditions with Perkin-Elmer Buffer II and Promega AmpliTaq DNA polymerase. Touch-down annealing temperatures started at 70° C. and ended at 60° C. (ΔT of −0.5° C. per cycle) for 20 cycles, followed by 15 cycles at 60° C. Products generated from 10 to 40 ng of template were separated on a 2.0% agarose gel. cDNA synthesis utilized random hexamer primers along with Superscript II (Life Technologies Inc., Gaithersburg, Md.). Subsequent PCR reactions were performed as above, except touch-down annealing temperatures were adjusted to 65 ° C.–55 ° C. The EMR primer, specific for the 3' portion of TRC8 was 5'-TCTTGTTAGCCAAAAGACTCG-3' (SEQ ID NO:21), whereas the F1 primer specific for FHIT exon 1 was 5'-TCCCTCTGCCTTTCATTCC-3' (SEQ ID NO:18).

Primers derived from the 5' coding portion of TRC8 yielded the expected product in the chromosome 8 only hybrid (lane 4) but not in a chromosome 3 only hybrid (lane 3). The same product was also present on the der(8), but not the der(3) chromosome from the 3;8 translocation (lanes 6 and 5, respectively). Similarly, the 8q24 YAC 880A9 (lane 7) was positive, as was a lambda clone, HD7 (lane 9), which contained both chromosome 8 and 3 material from the breakpoint junction. As noted above, the HD-7 genomic phage clone carrying the 3;8 translocation breakpoint (in particular, the breakpoint region from the der(8) chromosome) was isolated from a library prepared from the TL9944 cell line in λ FHXII (Stratagene, Inc., La Jolla, Calif.). A chromosome 3 probe (λ4040) which maps just distal to the 3;8 breakpoint was used for screening. Thus, the 5' coding region of TRC8 is proximal to the 8q24 breakpoint.

Southern blot analysis (See FIG. 4B) was used to demonstrate that the remaining 3' portion was contained on the der(3) chromosome (lane 5). Importantly, the probe hybridized to an altered band (arrow) in the der(3) hybrid consistent with the t(3;8) rearrangement. Together, these data indicate that TRC8 is localized to 8q24, is interrupted by the 3;8 translocation and that its 5' to 3' orientation is centromere to telomere (FIG. 1).

EXAMPLE 4

Expression of Both Reciprocal Products in (3;8) Lymphoblastoid Cells

To determine if both reciprocal products were expressed, RT(reverse transcriptase)-PCR analysis was performed on RNA isolated from TL9944 lymphoblastoid cells carrying the 3;8 translocation. Primers which flanked the breakpoint and were specific for the 5' and 3' portions of either TRC8 or FHIT (see FIG. 1) were used to demonstrate expression of both wild-type and fusion transcripts in TL9944 cells. As can be seen in FIG. 5, primers specific for wild-type FHIT and TRC8 generated bands of the expected size from both t(3;8) and control RNAs (lanes 1, 3, 5 and 7). In contrast, the primer pair R-M (5'-TRC8; SEQ ID NO:19) plus R1 (3'-FHIT; SEQ ID NO:12) produced a product only from the translocation cell line (lane 11) as did the primer pair F1 (5'-FHIT; SEQ ID NO:18) plus EMR (3'-TRC8; SEQ ID NO:21), lane 15. No products were observed in the absence of reverse transcriptase (even lanes). Sequence analysis (FIG. 5B) confirmed that the product from the der(8), 5'-TRC8/3'-FHIT, contained TRC8 sequences fused to FHIT exon 4. Similarly, the reciprocal product, 5'-FHIT/3'-TRC8, consisted of FHIT exon 3 fused to 3' TRC8 sequences. Thus, while FHIT is interrupted in its 5' untranslated region, its coding sequences are contained in the der(8) product. In contrast, TRC8 is interrupted within its coding sequence and, more specifically, within the predicted sterol sensing domain. Of note, a mutation in the sterol-sensing domain of SCAP enhances its activity and renders the molecule non-responsive to regulation by sterols (X. Hua, et al., *Cell* 87, 415 (1996)).

EXAMPLE 5

Identification of Tumor-Specific Mutation in TRC8 in Sporadic Renal Cell Carcinomas Single-stranded conformational polymorphism (SSCP) was performed using twelve primer pairs covering the coding sequence and the 5' untranslated region in 32 renal carcinomas. The SSCP analysis was performed by the method of Spritz et al. (R. A. Spritz, et al., *Am. J. Hum. Genet.* 51 1058–1065 (1992)). Nine primer sets (sets 1–9) were designed to amplify the entire coding region in segments averaging 325 bp and that also would span any intron-exon boundaries (see Table I). In addition, three primer sets (Set P1–P3) were designed to amplify the 5' untranslated region (see Table I).

TABLE I

| PRIMER SET | PRIMER NAME | SEQUENCE | SEQ ID NO: |
|---|---|---|---|
| Primers Specific for TRC8 Coding Region | | | |
| Set 1 | Set 1F | AGTTGCCCGCCTTAGCC | SEQ ID NO:22 |
| Set 1 | Set 1R | CCAAAGACACATACTCGACCC | SEQ ID NO:23 |
| Set 2 | Set 2F | CATAACTCTTAGTGGGGAAACATTC | SEQ ID NO:24 |
| Set 2 | Set 2R | TGTAACGTATCCAATTCCAAATG | SEQ ID NO:25 |
| Set 3 | Set 3F | TGGCACTTATCGTTCTACAGC | SEQ ID NO:26 |
| Set 3 | Set 3R | TCTTGTTAGCCAAAAGACTCG | SEQ ID NO:27 |
| Set 4 | Set 4F | AGTGTTTGTCCTGGCAGTG | SEQ ID NO:28 |
| Set 4 | Set 4R | ACAGTTAGTGTAGAATCGCACCC | SEQ ID NO:29 |
| Set 5 | Set 5F | TGGCAAATGAAACTGATTCC | SEQ ID NO:30 |
| Set 5 | Set 5R | CATGGATAAAATGCAGGACTG | SEQ ID NO:31 |
| Set 6 | Set 6F | AAGACCAGAAGAGAGACTTATTCG | SEQ ID NO:32 |
| Set 6 | Set 6R | TGCTGTAACTGCAAACAACC | SEQ ID NO:33 |
| Set 7 | Set 7F | TCTTTGGCATCACTATGCAC | SEQ ID NO:34 |
| Set 7 | Set 7R | CTTCACAGCAGTCCTACGATTC | SEQ ID NO:35 |
| Set 8 | Set 8F | CCAAAAATGGCTGGAAGAC | SEQ ID NO:36 |
| Set 8 | Set 8R | TGTCAGATTCAGCAGCAGC | SEQ ID NO:37 |
| Set 9 | Set 9F | CCACCCAATGAAACTCCAG | SEQ ID NO:38 |
| Set 9 | Set 9R | AGTAGCACATCACAGTAAACGG | SEQ ID NO:39 |
| Primers specific for 5' Untranslated Region of TRC8: | | | |
| Set P1 | Set P1F | TCCCAGGCAGCTCTGAAC | SEQ ID NO:40 |
| Set P1 | Set P1R | ACCATCTTGACCTCGCCC | SEQ ID NO:41 |
| Set P2 | Set P2F | GTTCGCTTGACTGACGGC | SEQ ID NO:42 |
| Set P2 | Set P2R | ATGAGCCGCTGCCACAC | SEQ ID NO:43 |
| Set P3 | Set P3F | CACCGAAACCCAGAGACC | SEQ ID NO:44 |
| Set P3 | Set P3R | CCAAAGACACATACTCGACCC | SEQ ID NO:45 |

These primers were used to amplify genomic DNA (10 ng) under touch-down conditions. Touch-down annealing temperatures started at 65 ° C. and ended at 55 ° C. (−T of −0.5° C. per cycle) for 20 cycles, followed by 15 cycles at 55 ° C. Because of the high GC content of the template, the PCR reactions contained 2.5 M betaine (W. Henke, et al., Nucleic Acids Res. 25, 3957 (1997)). Reaction products were mixed 50:50 with denaturing dyes (95% formamide, 10 mM NaOH, 20 mM EDTA, 0.02% bromophenol blue and 0.02% xylene cyanole) and heated to 95 ° C. for 5 min immediately before loading. Samples were separated at 8 W for 16 hr on 0.5×MDE (FMC) gels containing 0.6×Tris-borate buffer and 10% glycerol. Bands were visualized by silver staining.

Figure 6A:
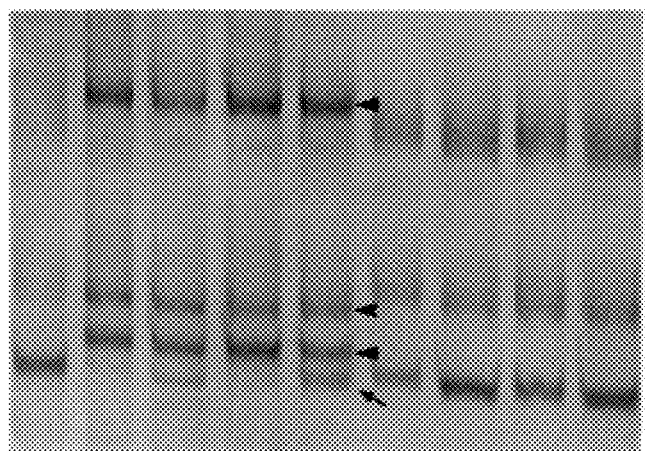
FIG. 6A illustrates the detection of a tumor-specific somatic mutation by Single Stranded Conformational Polymorphism Analysis (SSCP) and heteroduplex analysis. DNA samples were PCR amplified using primers flanking the first coding exon of TRC8 (M. Le Beau, et al. Genes Chromosomes Cancer 21, 281 (1998)). The products were denatured, separated on a non-denaturing MDE gel and detected by silver staining. Samples included matched tumor and normal DNAs from patients 1 and 7 (lanes 5–8, respectively) and an unrelated normal control (AG4103, lane 9). A separate SSCP gel was used to isolate four individual SSCP bands from RCC #1 (lane 5, marked by an arrow or arrow heads). The excised bands A to D corresponded to the indicated bands in lane 5 from top to bottom. These last templates were re-amplified and analyzed by SSCP to determine if they contained mutant or wild-type sequences. Comparison to lane 5 suggested that bands A and C contained primarily mutant DNA, band B was a mixture of mutant and wild-type and band D was wild-type only. The top and bottom panels show the SSCP and heteroduplex results, respectively.
Figure 6B:
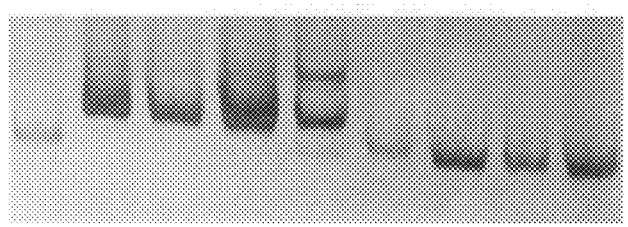
FIG. 6B illustrates that Renal Cell Carcinoma (RCC)#1 contains a 12 bp duplication in the 5' UTR. Purified PCR products shown in (A) (lanes 1 through 4) were sequenced. The mutation consisted of a 12 bp direct duplication (underlined) at bp position –73 (as numbered when the first base of the coding region is bp 1; this corresponds to bp 165 of SEQ ID NO:1.) which was present in the tumor sample but not the corresponding normal DNA. The repeat is from bp 165 to 176 of SEQ ID NO:7.

A duplication of 12 nucleotides in the 5' UTR was identified in Renal Cell Carcinoma (RCC) #1 (see FIG. 6A, lane 5) which was absent in matched normal DNA and thus tumor-specific. This mutation was verified by multiple separate PCR amplifications, SSCP analyses and sequencing, as well as by the use of an alternative primer set, thus eliminating the possibility of a PCR artifact. In the RCC #1 sample, very little of the wild-type heteroduplex product can be seen. This rearrangement resulted in an insertion of 12 bp in the tumor DNA (see FIG. 6B; bases 165 to 176 of SEQ ID NO:7), which was not present in the corresponding normal DNA of that patient. This insertion occurs in a consistently predicted stem-loop structure in the 5' untranslated region (the RNA stem loop structure was predicted by the GCG program MFOLD in both energetically optimal and suboptimal folds). The consequence of this insertion conceivably affects either transcription or translation. Although the frequency of TRC8 mutations in spontaneous tumors appears low, it is possible this finding is reminiscent of the mutation frequencies observed in BRCA1 and BRCA2 (P. A. Futreal, et al., Science 266, 120–122 (1994); J. M. Lancaster, et al., Nat. Genet. 13, 238–240 (1996)).

Although this example is described in relation to one specific mutation, it should be appreciated that the general approach set forth could be used to identify other mutations (including, for example, other insertions, or deletions, inversions and the like).

EXAMPLE 6

Amplification of TRC8 in a Sub-set of Variant Small Cell Lung Carcinomas

Figure 7:
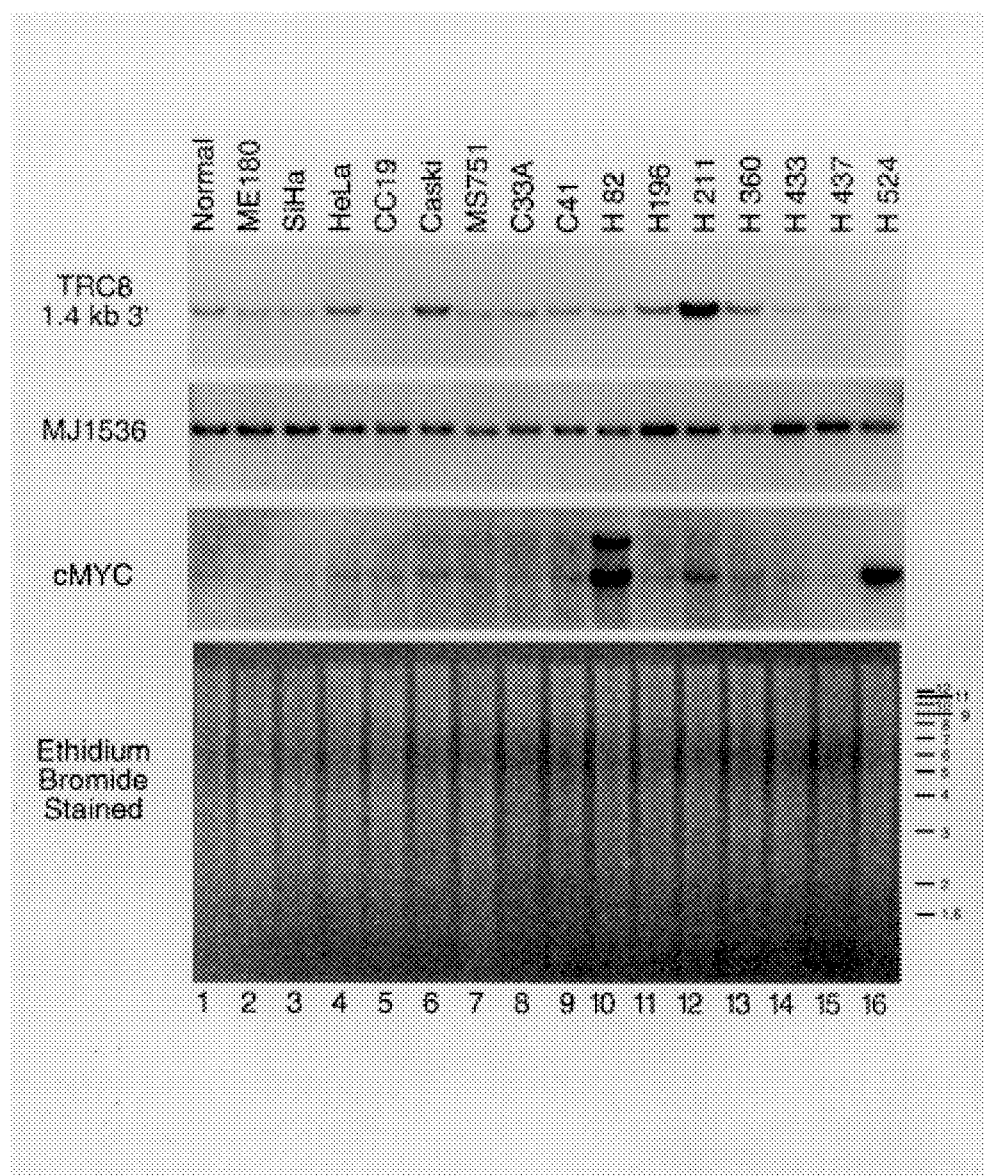
FIG. 7 demonstrates that TRC8 is amplified in a sub-set of variant Small Cell Lung Carcinomas (SCLCs). A Southern blot of EcoRI digested tumor cell line DNAs was prepared with nearly identical amounts of DNA (2 Tg) loaded in each lane, as determined by ethidium bromide fluorescence (bottom panel). The cell lines included 8 cervical carcinomas (ME18O, SiHa, HeLa, CC19, Caski, MS751, C33A and C41) and 7 small cell lung carcinomas of the variant sub-type (H82, H196, H211, H360, H433, H437 and H524), as indicated. The filter was hybridized sequentially with probes for TRC8 (top panel), a control locus on 3q (MJ 1536, second panel) and a genomic probe (380j9) which derives from within the cMYC locus (third panel). The autoradiogram generated by TRC8 was densitometrically scanned and band intensities were normalized by comparison to the control (lane 1). TRC8 is amplified 6-fold over normal in line H211 (lane 12).

Using Southern blot techniques, it was also shown that TRC8 underwent a significant (6-fold) amplification in 1 of the 7 variant small-cell lung carcinoma cell lines which were tested (see FIG. 7). From available YAC contig data (http://www-genome.wi.mit.edu), it was observed that 3 intervening YACs are required to link TRC8 (880A9) and cMYC (934E1), thus the distance separating these genes must be on the order of 2–3 Mb. To determine if the copy number increase resulted from coamplification of cMYC, the same blot was re-hybridized with the 380j9 probe from this locus (26). While cMYC was amplified in two variant SCLC lines (H82 and H524, lanes 10 and 16, respectively), it was only slightly increased in H211 (lane 12). These results indicate that TRC8 may be amplified independently of MYC and suggest that TRC8 gain of function may be important for tumorigenesis.

EXAMPLE 7

Synthesis of TRC8 Protein

The TRC8 protein was synthesized using the Promega in vitro transcription/translation (TNT) kit. On ice, 25 ul of the TNT rabbit reticulocyte lysate were mixed with 2 ul of TNT reaction buffer, 1 ul of RNA polymerase (T3 for sense; T7 for control antisense), 1 ul of the amino acid mixture, 2 ul of 35S-methionine (1000 Ci/mMole), 1 ul of RNasin RNAase inhibitor (40U/ul), 2 ul of the TRC8 cloned template (p45-1) and water to 50 ul total volume. Reactions were placed at 30 ° C. for 90 minutes. The reaction products were mixed 50:50 with laemmli SDS sample buffer and resolved on 7.0% SDS-polyacrylamide gels. It is critical to NOT heat denature the TRC8 protein as this leads to irreversible aggregation and failure of gel resolution methods. The gels were fixed in 10% acetic acid (30 min), neutralized with 0.1 M NaOH for 10 min, impregnated with 1M Na-salicylate and dried. Dried gels were exposed to Kodak X-omat AR film without screens for 2 h to overnight.

EXAMPLE 8

Diagnostic Applications

As noted above, evidence that various translocation events and mutations involving TRC8 appear to be associated with different tumors and cancers make the detection of alterations to TRC8 a potentially useful diagnostic tool. Diagnostic methods for identifying alterations could involve several different approaches including, for example, direct mutation detection using TRC8 specific primers (for instance, those set forth as SEQ ID NO:19–45, inclusively). The SSCP methodology described in Example 5 is also a useful approach.

Since the present invention is described with specific reference to the 3;8 translocation, methods for detecting their translocation event are described below with regards to this particular translocation. It should be appreciated, however, that these approaches have more general utility in detecting alterations to TRC8.

Thus, for example, the TRC8/FHIT and reciprocal FHIT/TRC8 fusions of the present invention can be used to determine the presence or absence of chromosomal translocations within cells suspected of being tumorous, especially within renal and thyroid cells Thus, the present invention can use PCR and DNA probes such as described above or YACs, cosmids and plasmids harboring the fused site to identify t(3;8) in renal and thyroid cells. PCR has several advantages as a tool for identifying t(3;8). PCR is rapid, sensitive and less affected by the quality of the samples as compared to chromosome methods such as FISH and karyotyping.

YACs and cosmids, however, can also be used as alternative diagnostic tools and have certain advantages as well. The YACs or cosmids can be quite specific since they preferably contain the fused site associated with the translocation. They may also yield a positive result in rare cases where PCR gives a negative result given that the YACs and cosmids contain a large region of the chromosome. Plasmids containing the DNA from the fused site can be used as probes to detect the translocation by various hybridization methods, such as Southern blots for example.

PCR analysis of the translocation involves standard methods. RNA is isolated from cells according to standard protocols. cDNA is formed from the RNA template using reverse transcriptase. Using the cDNA and primers specific for the t(3;8) such as described above, PCR is used to amplify the desired sequence. For example, a set of primers in which one primer binds at a point 5' to the breakpoint and the second primer binds 3' to the breakpoint could be used to amplify the intervening sequence. The PCR products formed are separated by agarose gel electrophoresis and visualized by well-known methods such as UV illumination after ethidium bromide staining.

FISH can also be performed according to methods known to those skilled in the art. Typically, YACs or cosmid DNA can be labeled with biotin. Metaphase chromosomes can be prepared from desired cells. The biotin-labeled probes are then allowed to hybridize with the chromosomes in the sample. The location of the hybridized areas can be detected using avidin with fluorescence tags and appropriate antibodies.

Southern blot hybridization can be performed by first isolating DNA from a patient's cells. The DNA is then digested with restriction endonucleases, the DNA fragments separated by gel electrophoresis and the fragments then transferred to nylon membranes. Various radio-labeled probes such as plasmids which contain the fused site can then be used to hybridize to DNA containing the breakpoint. Hybridization of the probe to DNA within the sample is typically done by autoradiography.

All the references listed herein, including, but not limited to patents and publications, are hereby incorporated by reference in their entirety.

---

We claim:

1. A method for producing a polypeptide comprising the amino acid sequence of SEQ ID NO: 2, said method comprising the steps of:

(a) culturing a host cell containing a vector comprising a nucleic acid molecule encoding the polypeptide under conditions suitable for the expression of the polypeptide; and (b) recovering the polypeptide from the host cell culture.

2. A polypeptide product of the expression in a host cell of a DNA according to a method that comprises:

(a) culturing a host cell containing a vector comprising a nucleic acid molecule encoding the polypeptide comprising the amino acid sequence of SEQ ID NO: 2; and (b) recovering the polypeptide from the host cell culture.

* * * * *

SEQUENCE LISTING

```
<160> NUMBER OF SEQ ID NOS:  46

<210> SEQ ID NO 1
<211> LENGTH: 2505
<212> TYPE: DNA
<213> ORGANISM: Homo sapiens
<220> FEATURE:
<221> NAME/KEY: CDS
<222> LOCATION: (238)..(2232)

<400> SEQUENCE: 1
gaaacccaga gacctcctgg ggagccgccg ccgccgccct ctcggccatc gctgcctccg         60
ccgcctgctc cacctcgagg gacgcgagcg ggcggcgggg ctggccgtga gagagacagg        120
```

```
                                                    -continued agaggaagga gggcagggcc ggagttgccc gccttagccc ccgccccgg ccgcggcccc      180 gggccctgcc ccgcgcggcc ctgccggcc caccgagccc tggtgtggca gcggctc         237 atg gcg gcc gtg ggg ccc ccg cag cag cag gtg cgg atg gcc cat cag      285
Met Ala Ala Val Gly Pro Pro Gln Gln Gln Val Arg Met Ala His Gln
 1               5                  10                  15 cag atc tgg gcg gcg ctc gaa gtg gcg ctc cgg gtg ccc tgc ctt tac      333
Gln Ile Trp Ala Ala Leu Glu Val Ala Leu Arg Val Pro Cys Leu Tyr
             20                  25                  30 atc atc gac gcc atc ttc aac tcc tac ccg gat tcc agc caa agc cgg      381
Ile Ile Asp Ala Ile Phe Asn Ser Tyr Pro Asp Ser Ser Gln Ser Arg
         35                  40                  45 ttc tgc atc gtg ctc cag atc ttc ctc cgg ctc ttt ggt gta ttt gca      429
Phe Cys Ile Val Leu Gln Ile Phe Leu Arg Leu Phe Gly Val Phe Ala
     50                  55                  60 tcc agt att gtt ctg atc ttg tca caa cga tca ctt ttc aag ttt tac      477
Ser Ser Ile Val Leu Ile Leu Ser Gln Arg Ser Leu Phe Lys Phe Tyr
 65                  70                  75                  80 acg tac agc tca gcc ttt ctg tta gct gca act tca gtg ttg gtg aat      525
Thr Tyr Ser Ser Ala Phe Leu Leu Ala Ala Thr Ser Val Leu Val Asn
                 85                  90                  95 tat tat gct tct ttg cac att gac ttc tat ggt gcc tac aac acg tca      573
Tyr Tyr Ala Ser Leu His Ile Asp Phe Tyr Gly Ala Tyr Asn Thr Ser
            100                 105                 110 gct ttt gga att gag ctg ctt cct cga aaa ggt ccc tcg ctg tgg atg      621
Ala Phe Gly Ile Glu Leu Leu Pro Arg Lys Gly Pro Ser Leu Trp Met
        115                 120                 125 gca ctt atc gtt cta cag cta aca ttt gga att gga tac gtt aca cta      669
Ala Leu Ile Val Leu Gln Leu Thr Phe Gly Ile Gly Tyr Val Thr Leu
    130                 135                 140 ctc cag att cat tcc atc tat tca caa tta att att ttg gat ctc ttg      717
Leu Gln Ile His Ser Ile Tyr Ser Gln Leu Ile Ile Leu Asp Leu Leu
145                 150                 155                 160 gtt cct gta ata ggc tta atc aca gag cta cca tta cac atc aga gag      765
Val Pro Val Ile Gly Leu Ile Thr Glu Leu Pro Leu His Ile Arg Glu
                165                 170                 175 act tta ctg ttt act tct tcc ttg att ctc aca tta aat aca gtg ttt      813
Thr Leu Leu Phe Thr Ser Ser Leu Ile Leu Thr Leu Asn Thr Val Phe
            180                 185                 190 gtc ctg gca gtg aaa ctg aag tgg ttt tat tat tcc aca cga tat gtt      861
Val Leu Ala Val Lys Leu Lys Trp Phe Tyr Tyr Ser Thr Arg Tyr Val
        195                 200                 205 tat ctt ttg gtg agg cac atg tat cga att tat gga tta cag tta ttg      909
Tyr Leu Leu Val Arg His Met Tyr Arg Ile Tyr Gly Leu Gln Leu Leu
    210                 215                 220 atg gag gac aca tgg aag agg att cgt ttc cca gac ata cta cga gtc      957
Met Glu Asp Thr Trp Lys Arg Ile Arg Phe Pro Asp Ile Leu Arg Val
225                 230                 235                 240 ttt tgg cta aca aga gtt aca gct cag gct aca gtg tta atg tac atc     1005
Phe Trp Leu Thr Arg Val Thr Ala Gln Ala Thr Val Leu Met Tyr Ile
                245                 250                 255 tta agg atg gca aat gaa act gat tcc ttc ttt att tct tgg gat gat     1053
Leu Arg Met Ala Asn Glu Thr Asp Ser Phe Phe Ile Ser Trp Asp Asp
            260                 265                 270 ttt tgg gac ctc att tgc aat ctt ata att agt ggg tgc gat tct aca     1101
Phe Trp Asp Leu Ile Cys Asn Leu Ile Ile Ser Gly Cys Asp Ser Thr
        275                 280                 285 cta act gta ctg ggc atg agt gct gta att tcc tca gta gcc cat tat     1149
Leu Thr Val Leu Gly Met Ser Ala Val Ile Ser Ser Val Ala His Tyr
    290                 295                 300
```

-continued

```
ttg ggg ctt gga ata ttg gcc ttt att gga tca act gag gaa gat gac    1197
Leu Gly Leu Gly Ile Leu Ala Phe Ile Gly Ser Thr Glu Glu Asp Asp
305                 310                 315                 320 agg cgt ctt ggc ttt gtt gca cct gtt tta ttt ttt att ttg gct ctt    1245
Arg Arg Leu Gly Phe Val Ala Pro Val Leu Phe Phe Ile Leu Ala Leu
                325                 330                 335 cag act ggg tta agt ggg cta aga cca gaa gag aga ctt att cgc tta    1293
Gln Thr Gly Leu Ser Gly Leu Arg Pro Glu Glu Arg Leu Ile Arg Leu
            340                 345                 350 agt aga aac atg tgc ctt tta tta act gca gtc ctg cat ttt atc cat    1341
Ser Arg Asn Met Cys Leu Leu Leu Thr Ala Val Leu His Phe Ile His
        355                 360                 365 gga atg aca gac cct gta tta atg tct ctc agt gcc tct cat gtg tca    1389
Gly Met Thr Asp Pro Val Leu Met Ser Leu Ser Ala Ser His Val Ser
370                 375                 380 tct ttt cgt aga cat ttt cct gtg ctg ttt gtc tct gct tgc ctg ttt    1437
Ser Phe Arg Arg His Phe Pro Val Leu Phe Val Ser Ala Cys Leu Phe
385                 390                 395                 400 att ctt cct gtc tta ctc agt tat gtt ctt tgg cat cac tat gca cta    1485
Ile Leu Pro Val Leu Leu Ser Tyr Val Leu Trp His His Tyr Ala Leu
                405                 410                 415 aat aca tgg ttg ttt gca gtt aca gca ttt tgt gtg gaa ctg tgc tta    1533
Asn Thr Trp Leu Phe Ala Val Thr Ala Phe Cys Val Glu Leu Cys Leu
            420                 425                 430 aaa gta att gtt tct ctc act gtt tat acg tta ttc atg att gat ggc    1581
Lys Val Ile Val Ser Leu Thr Val Tyr Thr Leu Phe Met Ile Asp Gly
        435                 440                 445 tac tat aat gtc ctc tgg gaa aag ctt gac gat tat gtc tac tac gtt    1629
Tyr Tyr Asn Val Leu Trp Glu Lys Leu Asp Asp Tyr Val Tyr Tyr Val
450                 455                 460 cgt tca aca ggc agt att att gaa ttt ata ttt gga gtt gta atg ttt    1677
Arg Ser Thr Gly Ser Ile Ile Glu Phe Ile Phe Gly Val Val Met Phe
465                 470                 475                 480 gga aat ggg gct tac act atg atg ttt gag tcg gga agt aaa att cgg    1725
Gly Asn Gly Ala Tyr Thr Met Met Phe Glu Ser Gly Ser Lys Ile Arg
                485                 490                 495 gct ttt atg atg tgc cta cat gca tat ttt aac atc tac tta caa gcc    1773
Ala Phe Met Met Cys Leu His Ala Tyr Phe Asn Ile Tyr Leu Gln Ala
            500                 505                 510 aaa aat ggc tgg aag aca ttt atg aat cgt agg act gct gtg aag aaa    1821
Lys Asn Gly Trp Lys Thr Phe Met Asn Arg Arg Thr Ala Val Lys Lys
        515                 520                 525 att aat tca ctt cct gaa ata aaa ggg agc cgc tta caa gaa ata aat    1869
Ile Asn Ser Leu Pro Glu Ile Lys Gly Ser Arg Leu Gln Glu Ile Asn
530                 535                 540 gat gta tgt gca atc tgc tat cat gag ttt aca aca tct gct cgt att    1917
Asp Val Cys Ala Ile Cys Tyr His Glu Phe Thr Thr Ser Ala Arg Ile
545                 550                 555                 560 aca ccg tgt aat cat tat ttc cat gca ctt tgc ctt cgg aaa tgg ctg    1965
Thr Pro Cys Asn His Tyr Phe His Ala Leu Cys Leu Arg Lys Trp Leu
                565                 570                 575 tac att caa gat act tgt cca atg tgc cat cag aaa gta tac atc gaa    2013
Tyr Ile Gln Asp Thr Cys Pro Met Cys His Gln Lys Val Tyr Ile Glu
            580                 585                 590 gat gat atc aag gat aat tca aat gta tct aac aac aat gga ttt att    2061
Asp Asp Ile Lys Asp Asn Ser Asn Val Ser Asn Asn Asn Gly Phe Ile
        595                 600                 605
```

```
cca ccc aat gaa act cca gag gaa gct gta aga gaa gct gct gct gaa       2109
Pro Pro Asn Glu Thr Pro Glu Glu Ala Val Arg Glu Ala Ala Ala Glu
    610             615                 620 tct gac agg gaa ttg aac gaa gat gac agt aca gat tgt gat gat gat       2157
Ser Asp Arg Glu Leu Asn Glu Asp Asp Ser Thr Asp Cys Asp Asp Asp
625             630                 635                 640 gtt caa aga gaa aga aat gga gtg att cag cac aca ggc gca gca gct       2205
Val Gln Arg Glu Arg Asn Gly Val Ile Gln His Thr Gly Ala Ala Ala
                645                 650                 655 gaa gaa ttt aat gat gat act gac tga tgaaaatagc atttattaat             2252
Glu Glu Phe Asn Asp Asp Thr Asp
                660                 665 gattgaggta tttgtttaaa attcagttca tccaaaatgg agtaatatcc ttcaccttca     2312
gtgtgtaacc aagcacaaaa acagtatcaa tgttgaatct gtgaatggtt ttccgtttac     2372
tgtgatgtgc tactgtaaat atacctcttt aattacttct ggtctctttg gtgacctgtt     2432
taaatttgtg tacattattg tacatagaat aaaatgtttt cacatttta tgacaaaaaa      2492 aaaaaaaaaa aaa                                                        2505

<210> SEQ ID NO 2
<211> LENGTH: 664
<212> TYPE: PRT
<213> ORGANISM: Homo sapiens

<400> SEQUENCE: 2

Met Ala Ala Val Gly Pro Pro Gln Gln Gln Val Arg Met Ala His Gln
 1               5                  10                  15

Gln Ile Trp Ala Ala Leu Glu Val Ala Leu Arg Val Pro Cys Leu Tyr
            20                  25                  30

Ile Ile Asp Ala Ile Phe Asn Ser Tyr Pro Asp Ser Ser Gln Ser Arg
        35                  40                  45

Phe Cys Ile Val Leu Gln Ile Phe Leu Arg Leu Phe Gly Val Phe Ala
    50                  55                  60

Ser Ser Ile Val Leu Ile Leu Ser Gln Arg Ser Leu Phe Lys Phe Tyr
65                  70                  75                  80

Thr Tyr Ser Ser Ala Phe Leu Leu Ala Ala Thr Ser Val Leu Val Asn
                85                  90                  95

Tyr Tyr Ala Ser Leu His Ile Asp Phe Tyr Gly Ala Tyr Asn Thr Ser
            100                 105                 110

Ala Phe Gly Ile Glu Leu Leu Pro Arg Lys Gly Pro Ser Leu Trp Met
        115                 120                 125

Ala Leu Ile Val Leu Gln Leu Thr Phe Gly Ile Gly Tyr Val Thr Leu
    130                 135                 140

Leu Gln Ile His Ser Ile Tyr Ser Gln Leu Ile Ile Leu Asp Leu Leu
145                 150                 155                 160

Val Pro Val Ile Gly Leu Ile Thr Glu Leu Pro Leu His Ile Arg Glu
                165                 170                 175

Thr Leu Leu Phe Thr Ser Ser Leu Ile Leu Thr Leu Asn Thr Val Phe
            180                 185                 190

Val Leu Ala Val Lys Leu Lys Trp Phe Tyr Ser Thr Arg Tyr Val
        195                 200                 205

Tyr Leu Leu Val Arg His Met Tyr Arg Ile Tyr Gly Leu Gln Leu Leu
    210                 215                 220

Met Glu Asp Thr Trp Lys Arg Ile Arg Phe Pro Asp Ile Leu Arg Val
225                 230                 235                 240
```

-continued

```
Phe Trp Leu Thr Arg Val Thr Ala Gln Ala Thr Val Leu Met Tyr Ile
            245                 250                 255

Leu Arg Met Ala Asn Glu Thr Asp Ser Phe Phe Ile Ser Trp Asp Asp
            260                 265                 270

Phe Trp Asp Leu Ile Cys Asn Leu Ile Ile Ser Gly Cys Asp Ser Thr
            275                 280                 285

Leu Thr Val Leu Gly Met Ser Ala Val Ile Ser Val Ala His Tyr
            290                 295                 300

Leu Gly Leu Gly Ile Leu Ala Phe Ile Gly Ser Thr Glu Glu Asp Asp
305                 310                 315                 320

Arg Arg Leu Gly Phe Val Ala Pro Val Leu Phe Phe Ile Leu Ala Leu
                325                 330                 335

Gln Thr Gly Leu Ser Gly Leu Arg Pro Glu Arg Leu Ile Arg Leu
            340                 345                 350

Ser Arg Asn Met Cys Leu Leu Leu Thr Ala Val Leu His Phe Ile His
            355                 360                 365

Gly Met Thr Asp Pro Val Leu Met Ser Leu Ser Ala Ser His Val Ser
    370                 375                 380

Ser Phe Arg Arg His Phe Pro Val Leu Phe Val Ser Ala Cys Leu Phe
385                 390                 395                 400

Ile Leu Pro Val Leu Leu Ser Tyr Val Leu Trp His His Tyr Ala Leu
                405                 410                 415

Asn Thr Trp Leu Phe Ala Val Thr Ala Phe Cys Val Glu Leu Cys Leu
                420                 425                 430

Lys Val Ile Val Ser Leu Thr Val Tyr Thr Leu Phe Met Ile Asp Gly
                435                 440                 445

Tyr Tyr Asn Val Leu Trp Glu Lys Leu Asp Asp Tyr Val Tyr Tyr Val
    450                 455                 460

Arg Ser Thr Gly Ser Ile Ile Glu Phe Ile Phe Gly Val Val Met Phe
465                 470                 475                 480

Gly Asn Gly Ala Tyr Thr Met Met Phe Glu Ser Gly Ser Lys Ile Arg
                485                 490                 495

Ala Phe Met Met Cys Leu His Ala Tyr Phe Asn Ile Tyr Leu Gln Ala
                500                 505                 510

Lys Asn Gly Trp Lys Thr Phe Met Asn Arg Arg Thr Ala Val Lys Lys
                515                 520                 525

Ile Asn Ser Leu Pro Glu Ile Lys Gly Ser Arg Leu Gln Glu Ile Asn
            530                 535                 540

Asp Val Cys Ala Ile Cys Tyr His Glu Phe Thr Thr Ser Ala Arg Ile
545                 550                 555                 560

Thr Pro Cys Asn His Tyr Phe His Ala Leu Cys Leu Arg Lys Trp Leu
                565                 570                 575

Tyr Ile Gln Asp Thr Cys Pro Met Cys His Gln Lys Val Tyr Ile Glu
            580                 585                 590

Asp Asp Ile Lys Asp Asn Ser Asn Val Ser Asn Asn Gly Phe Ile
            595                 600                 605

Pro Pro Asn Glu Thr Pro Glu Glu Ala Val Arg Glu Ala Ala Ala Glu
    610                 615                 620

Ser Asp Arg Glu Leu Asn Glu Asp Asp Ser Thr Asp Cys Asp Asp Asp
625                 630                 635                 640

Val Gln Arg Glu Arg Asn Gly Val Ile Gln His Thr Gly Ala Ala Ala
                645                 650                 655
```

```
Glu Glu Phe Asn Asp Asp Thr Asp
            660
```

<210> SEQ ID NO 3
<211> LENGTH: 1286
<212> TYPE: PRT
<213> ORGANISM: Drosophila melanogaster

<400> SEQUENCE: 3

```
Met Asp Arg Asp Ser Leu Pro Arg Val Pro Asp Thr His Gly Asp Val
  1               5                  10                  15

Val Asp Glu Lys Leu Phe Ser Asp Leu Tyr Ile Arg Thr Ser Trp Val
             20                  25                  30

Asp Ala Gln Val Ala Leu Asp Gln Ile Asp Lys Gly Lys Ala Arg Gly
         35                  40                  45

Ser Arg Thr Ala Ile Tyr Leu Arg Ser Val Phe Gln Ser His Leu Glu
     50                  55                  60

Thr Leu Gly Ser Ser Val Gln Lys His Ala Gly Lys Val Leu Phe Val
 65                  70                  75                  80

Ala Ile Leu Val Leu Ser Thr Phe Cys Val Gly Leu Lys Ser Ala Gln
                 85                  90                  95

Ile His Ser Lys Val His Gln Leu Trp Ile Gln Glu Gly Gly Arg Leu
            100                 105                 110

Glu Ala Glu Leu Ala Tyr Thr Gln Lys Thr Ile Gly Glu Asp Glu Ser
        115                 120                 125

Ala Thr His Gln Leu Leu Ile Gln Thr Thr His Asp Pro Asn Ala Ser
    130                 135                 140

Val Leu His Pro Gln Ala Leu Leu Ala His Leu Glu Val Leu Val Lys
145                 150                 155                 160

Ala Thr Ala Val Lys Val His Leu Tyr Asp Thr Glu Trp Gly Leu Arg
                165                 170                 175

Asp Met Cys Asn Met Pro Ser Thr Pro Ser Phe Glu Gly Ile Tyr Tyr
            180                 185                 190

Ile Glu Gln Ile Leu Arg His Leu Pro Cys Ser Ile Ile Thr Pro
        195                 200                 205

Leu Asp Cys Phe Trp Glu Gly Ser Gln Leu Leu Gly Pro Glu Ser Ala
    210                 215                 220

Val Val Ile Pro Gly Leu Asn Gln Arg Leu Leu Trp Thr Thr Leu Asn
225                 230                 235                 240

Pro Ala Ser Val Met Gln Tyr Met Lys Gln Lys Met Ser Glu Glu Lys
                245                 250                 255

Ile Ser Phe Asp Phe Glu Thr Val Glu Gln Tyr Met Lys Arg Ala Ala
            260                 265                 270

Ile Gly Ser Gly Tyr Met Glu Lys Pro Cys Leu Asn Pro Leu Asn Pro
        275                 280                 285

Asn Cys Pro Asp Thr Ala Pro Asn Lys Asn Ser Thr Gln Pro Pro Asp
    290                 295                 300

Val Gly Ala Ile Leu Ser Gly Gly Cys Tyr Gly Tyr Ala Ala Lys His
305                 310                 315                 320

Met His Trp Pro Glu Glu Leu Ile Val Gly Gly Arg Lys Arg Asn Arg
                325                 330                 335

Ser Gly His Leu Arg Lys Ala Gln Ala Leu Gln Ser Val Val Gln Leu
            340                 345                 350

Met Thr Glu Lys Glu Met Tyr Asp Gln Trp Gln Asp Asn Tyr Lys Val
        355                 360                 365
```

-continued

```
His His Leu Gly Trp Thr Gln Glu Lys Ala Ala Glu Val Leu Asn Ala
    370                 375                 380

Trp Gln Arg Asn Phe Ser Arg Glu Val Glu Gln Leu Leu Arg Lys Gln
385                 390                 395                 400

Ser Arg Ile Ala Thr Asn Tyr Asp Ile Tyr Val Phe Ser Ser Ala Ala
            405                 410                 415

Leu Asp Asp Ile Leu Ala Lys Phe Ser His Pro Ser Ala Leu Ser Ile
                420                 425                 430

Val Ile Gly Val Ala Val Thr Val Leu Tyr Ala Phe Cys Thr Leu Leu
            435                 440                 445

Arg Trp Arg Asp Pro Val Arg Gly Gln Ser Ser Val Gly Val Ala Gly
450                 455                 460

Val Leu Leu Met Cys Phe Ser Thr Ala Ala Gly Leu Gly Leu Ser Ala
465                 470                 475                 480

Leu Leu Gly Ile Val Phe Asn Ala Ala Ser Thr Gln Val Val Pro Phe
                485                 490                 495

Leu Ala Leu Gly Leu Gly Val Asp His Ile Phe Met Leu Thr Ala Ala
            500                 505                 510

Tyr Ala Glu Ser Asn Arg Arg Glu Gln Thr Lys Leu Ile Leu Lys Lys
            515                 520                 525

Val Gly Pro Ser Ile Leu Phe Ser Ala Cys Ser Thr Ala Gly Ser Phe
530                 535                 540

Phe Ala Ala Ala Phe Ile Pro Val Pro Ala Leu Lys Val Phe Cys Leu
545                 550                 555                 560

Gln Ala Ala Ile Val Met Cys Ser Asn Leu Ala Ala Ala Leu Leu Val
                565                 570                 575

Phe Pro Ala Met Ile Ser Leu Asp Leu Arg Arg Arg Thr Ala Gly Arg
            580                 585                 590

Ala Asp Ile Phe Cys Cys Cys Phe Pro Val Trp Lys Glu Gln Pro Lys
            595                 600                 605

Val Ala Pro Pro Val Leu Pro Leu Asn Asn Asn Gly Arg Gly Ala
    610                 615                 620

Arg His Pro Lys Ser Cys Asn Asn Arg Val Pro Leu Pro Ala Gln
625                 630                 635                 640

Asn Pro Leu Leu Glu Gln Arg Ala Asp Ile Pro Gly Ser Ser His Ser
            645                 650                 655

Leu Ala Ser Phe Ser Leu Ala Thr Phe Ala Phe Gln His Tyr Thr Pro
            660                 665                 670

Phe Leu Met Arg Ser Trp Val Lys Phe Leu Thr Val Met Gly Phe Leu
            675                 680                 685

Ala Ala Leu Ile Ser Ser Leu Tyr Ala Ser Thr Arg Leu Gln Asp Gly
            690                 695                 700

Leu Asp Ile Ile Asp Leu Val Pro Lys Asp Ser Asn Glu His Lys Phe
705                 710                 715                 720

Leu Asp Ala Gln Thr Arg Leu Phe Gly Phe Tyr Ser Met Tyr Ala Val
                725                 730                 735

Thr Gln Gly Asn Phe Glu Tyr Pro Thr Gln Gln Leu Leu Arg Asp
            740                 745                 750

Tyr His Asp Ser Phe Val Arg Val Pro His Val Ile Lys Asn Asp Asn
    755                 760                 765

Gly Gly Leu Pro Asp Phe Trp Leu Leu Leu Phe Ser Glu Trp Leu Gly
770                 775                 780
```

-continued

```
Asn Leu Gln Lys Ile Phe Asp Glu Glu Tyr Arg Asp Gly Arg Leu Thr
785                 790                 795                 800

Lys Glu Cys Trp Phe Pro Asn Ala Ser Ser Asp Ala Ile Leu Ala Tyr
                805                 810                 815

Lys Leu Ile Val Gln Thr Gly His Val Asp Asn Pro Val Asp Lys Glu
                820                 825                 830

Leu Val Leu Thr Asn Arg Leu Val Asn Ser Asp Gly Ile Ile Asn Gln
                835                 840                 845

Arg Ala Phe Tyr Asn Tyr Leu Ser Ala Trp Ala Thr Asn Asp Val Phe
850                 855                 860

Ala Tyr Gly Ala Ser Gln Gly Lys Leu Tyr Pro Glu Pro Arg Gln Tyr
865                 870                 875                 880

Phe His Gln Pro Asn Glu Tyr Asp Leu Lys Ile Pro Lys Ser Leu Pro
                885                 890                 895

Leu Val Tyr Ala Gln Met Pro Phe Tyr Leu His Gly Leu Thr Asp Thr
                900                 905                 910

Ser Gln Ile Lys Thr Leu Ile Gly His Ile Arg Asp Leu Ser Val Lys
                915                 920                 925

Tyr Glu Gly Phe Gly Leu Pro Asn Tyr Pro Ser Gly Ile Pro Phe Ile
930                 935                 940

Phe Trp Glu Gln Tyr Met Thr Leu Arg Ser Ser Leu Ala Met Ile Leu
945                 950                 955                 960

Ala Cys Val Leu Leu Ala Ala Leu Val Leu Ser Leu Leu Leu
                965                 970                 975

Ser Val Trp Ala Ala Val Leu Val Ile Leu Ser Val Leu Ala Ser Leu
                980                 985                 990

Ala Gln Ile Phe Gly Ala Met Thr Leu Leu Gly Ile Lys Leu Ser Ala
                995                 1000                1005

Ile Pro Ala Val Ile Leu Ile Leu Ser Val Gly Met Met Leu Cys Phe
    1010                1015                1020

Asn Val Leu Ile Ser Leu Gly Phe Met Thr Ser Val Gly Asn Arg Gln
1025                1030                1035                1040

Arg Arg Val Gln Leu Ser Met Gln Met Ser Leu Gly Pro Leu Val His
                1045                1050                1055

Gly Met Leu Thr Ser Gly Val Ala Val Phe Met Leu Ser Thr Ser Pro
            1060                1065                1070

Phe Glu Phe Val Ile Arg His Phe Cys Trp Leu Leu Leu Val Val Leu
            1075                1080                1085

Cys Val Gly Ala Cys Asn Ser Leu Leu Val Phe Pro Ile Leu Leu Ser
    1090                1095                1100

Met Val Gly Pro Glu Ala Glu Leu Val Pro Leu Glu His Pro Asp Arg
1105                1110                1115                1120

Ile Ser Thr Pro Ser Pro Leu Pro Val Arg Ser Ser Lys Arg Ser Gly
                1125                1130                1135

Lys Ser Tyr Val Val Gln Gly Ser Arg Ser Ser Arg Gly Ser Cys Gln
                1140                1145                1150

Lys Ser His His His His Lys Asp Leu Asn Asp Pro Ser Leu Thr
                1155                1160                1165

Thr Ile Thr Glu Glu Pro Gln Ser Trp Lys Ser Ser Asn Ser Ser Ile
    1170                1175                1180

Gln Met Pro Asn Asp Trp Thr Tyr Gln Pro Arg Glu Gln Arg Pro Ala
1185                1190                1195                1200
```

-continued

```
Ser Tyr Ala Ala Pro Pro Ala Tyr His Lys Ala Ala Gln Gln
        1205            1210            1215

His His Gln His Gln Gly Pro Thr Thr Pro Pro Pro Phe Pro
        1220            1225            1230

Thr Ala Tyr Pro Pro Glu Leu Gln Ser Ile Val Val Gln Pro Glu Val
        1235            1240            1245

Thr Val Glu Thr Thr His Ser Asp Ser Asn Thr Thr Lys Val Thr Ala
    1250            1255            1260

Thr Ala Asn Ile Lys Val Glu Leu Ala Met Pro Gly Arg Ala Val Arg
1265            1270            1275            1280

Ser Tyr Asn Phe Thr Ser
        1285

<210> SEQ ID NO 4
<211> LENGTH: 888
<212> TYPE: PRT
<213> ORGANISM: Homo sapiens

<400> SEQUENCE: 4

Met Leu Ser Arg Leu Phe Arg Met His Gly Leu Phe Val Ala Ser His
  1               5                  10                  15

Pro Trp Glu Val Ile Val Gly Thr Val Thr Leu Thr Ile Cys Met Met
             20                  25                  30

Ser Met Asn Met Phe Thr Gly Asn Asn Lys Ile Cys Gly Trp Asn Tyr
         35                  40                  45

Glu Cys Pro Lys Phe Glu Glu Asp Val Leu Ser Ser Asp Ile Ile Ile
     50                  55                  60

Leu Thr Ile Thr Arg Cys Ile Ala Ile Leu Tyr Ile Tyr Phe Gln Phe
 65                  70                  75                  80

Gln Asn Leu Arg Gln Leu Gly Ser Lys Tyr Ile Leu Gly Ile Ala Gly
                 85                  90                  95

Leu Phe Thr Ile Phe Ser Ser Phe Val Phe Ser Thr Val Val Ile His
            100                 105                 110

Phe Leu Asp Lys Glu Leu Thr Gly Leu Asn Glu Ala Leu Pro Phe Phe
        115                 120                 125

Leu Leu Leu Ile Asp Leu Ser Arg Ala Ser Thr Leu Ala Lys Phe Ala
    130                 135                 140

Leu Ser Ser Asn Ser Gln Asp Glu Val Arg Glu Asn Ile Ala Arg Gly
145                 150                 155                 160

Met Ala Ile Leu Gly Pro Thr Phe Thr Leu Asp Ala Leu Val Glu Cys
                165                 170                 175

Leu Val Ile Gly Val Gly Thr Met Ser Gly Val Arg Gln Leu Glu Ile
            180                 185                 190

Met Cys Cys Phe Gly Cys Met Ser Val Leu Ala Asn Tyr Phe Val Phe
        195                 200                 205

Met Thr Phe Phe Pro Ala Cys Val Ser Leu Val Leu Glu Leu Ser Arg
    210                 215                 220

Glu Ser Arg Glu Gly Arg Pro Ile Trp Gln Leu Ser His Phe Ala Arg
225                 230                 235                 240

Val Leu Glu Glu Glu Glu Asn Lys Pro Asn Pro Val Thr Gln Arg Val
                245                 250                 255

Lys Met Ile Met Ser Leu Gly Leu Val Leu Val His Ala His Ser Arg
            260                 265                 270

Trp Ile Ala Asp Pro Ser Pro Gln Asn Ser Thr Ala Asp Thr Ser Lys
        275                 280                 285
```

```
Val Ser Leu Gly Leu Asp Glu Asn Val Ser Lys Arg Ile Glu Pro Ser
    290                 295                 300
Val Ser Leu Trp Gln Phe Tyr Leu Ser Lys Met Ile Ser Met Asp Ile
305                 310                 315                 320
Glu Gln Val Ile Thr Leu Ser Leu Ala Leu Leu Ala Val Lys Tyr
                325                 330                 335
Ile Phe Phe Glu Gln Thr Glu Thr Glu Ser Thr Leu Ser Leu Lys Asn
                340                 345                 350
Pro Ile Thr Ser Pro Val Val Thr Gln Lys Val Pro Asp Asn Cys
            355                 360                 365
Cys Arg Arg Glu Pro Met Leu Val Arg Asn Asn Gln Lys Cys Asp Ser
    370                 375                 380
Val Glu Glu Glu Thr Gly Ile Asn Arg Glu Arg Lys Val Glu Val Ile
385                 390                 395                 400
Lys Pro Leu Val Ala Glu Thr Asp Thr Pro Asn Arg Ala Thr Phe Val
                405                 410                 415
Val Gly Asn Ser Ser Leu Leu Asp Thr Ser Ser Val Leu Val Thr Gln
            420                 425                 430
Glu Pro Glu Ile Glu Leu Pro Arg Glu Pro Arg Pro Asn Glu Glu Cys
            435                 440                 445
Leu Gln Ile Leu Gly Asn Ala Glu Lys Gly Ala Lys Phe Leu Ser Asp
    450                 455                 460
Ala Glu Ile Ile Gln Leu Val Asn Ala Lys His Ile Pro Ala Tyr Lys
465                 470                 475                 480
Leu Glu Thr Leu Met Glu Thr His Glu Arg Gly Val Ser Ile Arg Arg
                485                 490                 495
Gln Leu Leu Ser Lys Lys Leu Ser Glu Pro Ser Ser Leu Gln Tyr Leu
            500                 505                 510
Pro Tyr Arg Asp Tyr Asn Tyr Ser Leu Val Met Gly Ala Cys Cys Glu
            515                 520                 525
Asn Val Ile Gly Tyr Met Pro Ile Pro Val Gly Val Ala Gly Pro Leu
    530                 535                 540
Cys Leu Asp Glu Lys Glu Phe Gln Val Pro Met Ala Thr Thr Glu Gly
545                 550                 555                 560
Cys Leu Val Ala Ser Thr Asn Arg Gly Cys Arg Ala Ile Gly Leu Gly
                565                 570                 575
Gly Gly Ala Ser Ser Arg Val Leu Ala Asp Gly Met Thr Arg Gly Pro
            580                 585                 590
Val Val Arg Leu Pro Arg Ala Cys Asp Ser Ala Glu Val Lys Ala Trp
    595                 600                 605
Leu Glu Thr Ser Glu Gly Phe Ala Val Ile Lys Glu Ala Phe Asp Ser
610                 615                 620
Thr Ser Arg Phe Ala Arg Leu Gln Lys Leu His Thr Ser Ile Ala Gly
625                 630                 635                 640
Arg Asn Leu Tyr Ile Arg Phe Gln Ser Arg Ser Gly Asp Ala Met Gly
                645                 650                 655
Met Asn Met Ile Ser Lys Gly Thr Glu Lys Ala Leu Ser Lys Leu His
            660                 665                 670
Glu Tyr Phe Pro Glu Met Gln Ile Leu Ala Val Ser Gly Asn Tyr Cys
    675                 680                 685
Thr Asp Lys Lys Pro Ala Ala Ile Asn Trp Ile Glu Gly Arg Gly Lys
690                 695                 700
```

```
Ser Val Val Cys Glu Ala Val Ile Pro Ala Lys Val Val Arg Glu Val
705                 710                 715                 720

Leu Lys Thr Thr Thr Glu Ala Met Ile Glu Val Asn Ile Asn Lys Asn
            725                 730                 735

Leu Val Gly Ser Ala Met Ala Gly Ser Ile Gly Gly Tyr Asn Ala His
            740                 745                 750

Ala Ala Asn Ile Val Thr Ala Ile Tyr Ile Ala Cys Gly Gln Asp Ala
            755                 760                 765

Ala Gln Asn Val Gly Ser Ser Asn Cys Ile Thr Leu Met Glu Ala Ser
            770                 775                 780

Gly Pro Thr Asn Glu Asp Leu Tyr Ile Ser Cys Thr Met Pro Ser Ile
785                 790                 795                 800

Glu Ile Gly Thr Val Gly Gly Gly Thr Asn Leu Leu Pro Gln Gln Ala
                805                 810                 815

Cys Leu Gln Met Leu Gly Val Gln Gly Ala Cys Lys Asp Asn Pro Gly
                820                 825                 830

Glu Asn Ala Arg Gln Leu Ala Arg Ile Val Cys Gly Thr Val Met Ala
                835                 840                 845

Gly Glu Leu Ser Leu Met Ala Ala Leu Ala Ala Gly His Leu Val Lys
850                 855                 860

Ser His Met Ile His Asn Arg Ser Lys Ile Asn Leu Gln Asp Leu Gln
865                 870                 875                 880

Gly Ala Cys Thr Lys Lys Thr Ala
                885

<210> SEQ ID NO 5
<211> LENGTH: 1447
<212> TYPE: PRT
<213> ORGANISM: Homo sapiens

<400> SEQUENCE: 5

Met Ala Ser Ala Gly Asn Ala Ala Glu Pro Gln Asp Arg Gly Gly Gly
 1               5                  10                  15

Gly Ser Gly Cys Ile Gly Ala Pro Gly Arg Pro Ala Gly Gly Gly Arg
             20                  25                  30

Arg Arg Arg Thr Gly Gly Leu Arg Arg Ala Ala Pro Asp Arg Asp
         35                  40                  45

Tyr Leu His Arg Pro Ser Tyr Cys Asp Ala Ala Phe Ala Leu Glu Gln
     50                  55                  60

Ile Ser Lys Gly Lys Ala Thr Gly Arg Lys Ala Pro Leu Trp Leu Arg
 65                  70                  75                  80

Ala Lys Phe Gln Arg Leu Leu Phe Lys Leu Gly Cys Tyr Ile Gln Lys
                 85                  90                  95

Asn Cys Gly Lys Phe Leu Val Val Gly Leu Leu Ile Phe Gly Ala Phe
                100                 105                 110

Ala Val Gly Leu Lys Ala Ala Asn Leu Glu Thr Asn Val Glu Glu Leu
            115                 120                 125

Trp Val Glu Val Gly Gly Arg Val Ser Arg Glu Leu Asn Tyr Thr Arg
        130                 135                 140

Gln Lys Ile Gly Glu Glu Ala Met Phe Asn Pro Gln Leu Met Ile Gln
145                 150                 155                 160

Thr Pro Lys Glu Glu Gly Ala Asn Val Leu Thr Thr Glu Ala Leu Leu
                165                 170                 175

Gln His Leu Asp Ser Ala Leu Gln Ala Ser Arg Val His Val Tyr Met
            180                 185                 190
```

-continued

```
Tyr Asn Arg Gln Trp Lys Leu Glu His Leu Cys Tyr Lys Ser Gly Glu
            195                 200                 205

Leu Ile Thr Glu Thr Gly Tyr Met Asp Gln Ile Ile Glu Tyr Leu Tyr
    210                 215                 220

Pro Cys Leu Ile Ile Thr Pro Leu Asp Cys Phe Trp Glu Gly Ala Lys
225                 230                 235                 240

Leu Gln Ser Gly Thr Ala Tyr Leu Leu Gly Lys Pro Pro Leu Arg Trp
                245                 250                 255

Thr Asn Phe Asp Pro Leu Glu Phe Leu Glu Glu Leu Lys Lys Ile Asn
            260                 265                 270

Tyr Gln Val Asp Ser Trp Glu Glu Met Leu Asn Lys Ala Glu Val Gly
            275                 280                 285

His Gly Tyr Met Asp Arg Pro Cys Leu Asn Pro Ala Asp Pro Asp Cys
            290                 295                 300

Pro Ala Thr Ala Pro Asn Lys Asn Ser Thr Lys Pro Leu Asp Met Ala
305                 310                 315                 320

Leu Val Leu Asn Gly Gly Cys His Gly Leu Ser Arg Lys Tyr Met His
                325                 330                 335

Trp Gln Glu Glu Leu Ile Val Gly Gly Thr Val Lys Asn Ser Thr Gly
            340                 345                 350

Lys Leu Val Ser Ala His Ala Leu Gln Thr Met Phe Gln Leu Met Thr
            355                 360                 365

Pro Lys Gln Met Tyr Glu His Phe Lys Gly Tyr Glu Tyr Val Ser His
            370                 375                 380

Ile Asn Trp Asn Glu Asp Lys Ala Ala Ala Ile Leu Glu Ala Trp Gln
385                 390                 395                 400

Arg Thr Tyr Val Glu Val Val His Gln Ser Val Ala Gln Asn Ser Thr
                405                 410                 415

Gln Lys Val Leu Ser Phe Thr Thr Thr Leu Asp Asp Ile Leu Lys
            420                 425                 430

Ser Phe Ser Asp Val Ser Val Ile Arg Val Ala Ser Gly Tyr Leu Leu
            435                 440                 445

Met Leu Ala Tyr Ala Cys Leu Thr Met Leu Arg Trp Asp Cys Ser Lys
    450                 455                 460

Ser Gln Gly Ala Val Gly Leu Ala Gly Val Leu Leu Val Ala Leu Ser
465                 470                 475                 480

Val Ala Ala Gly Leu Gly Leu Cys Ser Leu Ile Gly Ile Ser Phe Asn
                485                 490                 495

Ala Ala Thr Thr Gln Val Leu Pro Phe Leu Ala Leu Gly Val Gly Val
            500                 505                 510

Asp Asp Val Phe Leu Leu Ala His Ala Phe Ser Glu Thr Gly Gln Asn
            515                 520                 525

Lys Arg Ile Pro Phe Glu Asp Arg Thr Gly Glu Cys Leu Lys Arg Thr
            530                 535                 540

Gly Ala Ser Val Ala Leu Thr Ser Ile Ser Asn Val Thr Ala Phe Phe
545                 550                 555                 560

Met Ala Ala Leu Ile Pro Ile Pro Ala Leu Arg Ala Phe Ser Leu Gln
                565                 570                 575

Ala Ala Val Val Val Phe Asn Phe Ala Met Val Leu Leu Ile Phe
            580                 585                 590

Pro Ala Ile Leu Ser Met Asp Leu Tyr Arg Arg Glu Asp Arg Leu
            595                 600                 605
```

```
Asp Ile Phe Cys Cys Phe Thr Ser Pro Cys Val Ser Arg Val Ile Gln
    610                 615                 620
Val Glu Pro Gln Ala Tyr Thr Asp Thr His Asp Asn Thr Arg Tyr Ser
625                 630                 635                 640
Pro Pro Pro Pro Tyr Ser Ser His Ser Phe Ala His Glu Thr Gln Ile
                645                 650                 655
Thr Met Gln Ser Thr Val Gln Leu Arg Thr Glu Tyr Asp Pro His Thr
            660                 665                 670
His Val Tyr Tyr Thr Thr Ala Glu Pro Arg Ser Glu Ile Ser Val Gln
        675                 680                 685
Pro Val Thr Val Thr Gln Asp Thr Leu Ser Cys Gln Ser Pro Glu Ser
    690                 695                 700
Thr Ser Ser Thr Arg Asp Leu Leu Ser Gln Phe Ser Asp Ser Ser Leu
705                 710                 715                 720
His Cys Leu Glu Pro Pro Cys Thr Lys Trp Thr Leu Ser Ser Phe Ala
                725                 730                 735
Glu Lys His Tyr Ala Pro Phe Leu Leu Lys Pro Lys Ala Lys Val Val
            740                 745                 750
Val Ile Phe Leu Phe Leu Gly Leu Leu Gly Val Ser Leu Tyr Gly Thr
        755                 760                 765
Thr Arg Val Arg Asp Gly Leu Asp Leu Thr Asp Ile Val Pro Arg Glu
    770                 775                 780
Thr Arg Glu Tyr Asp Phe Ile Ala Ala Gln Phe Lys Tyr Phe Ser Phe
785                 790                 795                 800
Tyr Asn Met Tyr Ile Val Thr Gln Lys Ala Asp Tyr Pro Asn Ile Gln
                805                 810                 815
His Leu Leu Tyr Asp Leu His Arg Ser Phe Ser Asn Val Lys Tyr Val
            820                 825                 830
Met Leu Glu Glu Asn Lys Gln Leu Pro Lys Met Trp Leu His Tyr Phe
        835                 840                 845
Arg Asp Trp Leu Gln Gly Leu Gln Asp Ala Phe Asp Ser Asp Trp Glu
    850                 855                 860
Thr Gly Lys Ile Met Pro Asn Asn Tyr Lys Asn Gly Ser Asp Asp Gly
865                 870                 875                 880
Val Leu Ala Tyr Lys Leu Leu Val Gln Thr Gly Ser Arg Asp Lys Pro
                885                 890                 895
Ile Asp Ile Ser Gln Leu Thr Lys Gln Arg Leu Val Asp Ala Asp Gly
            900                 905                 910
Ile Ile Asn Pro Ser Ala Phe Tyr Ile Tyr Leu Thr Ala Trp Val Ser
        915                 920                 925
Asn Asp Pro Val Ala Tyr Ala Ala Ser Gln Ala Asn Ile Arg Pro His
    930                 935                 940
Arg Pro Glu Trp Val His Asp Lys Ala Asp Tyr Met Pro Glu Thr Arg
945                 950                 955                 960
Leu Arg Ile Pro Ala Ala Glu Pro Ile Glu Tyr Ala Gln Phe Pro Phe
                965                 970                 975
Tyr Leu Asn Gly Leu Arg Asp Thr Ser Asp Phe Val Glu Ala Ile Glu
            980                 985                 990
Lys Val Arg Thr Ile Cys Ser Asn Tyr Thr Ser Leu Gly Leu Ser Ser
        995                 1000                1005
Tyr Pro Asn Gly Tyr Pro Phe Leu Phe Trp Glu Gln Tyr Ile Gly Leu
    1010                1015                1020
```

-continued

```
Arg His Trp Leu Leu Leu Phe Ile Ser Val Val Leu Ala Cys Thr Phe
1025                1030                1035                1040

Leu Val Cys Ala Val Phe Leu Leu Asn Pro Trp Thr Ala Gly Ile Ile
            1045                1050                1055

Val Met Val Leu Ala Leu Met Thr Val Glu Leu Phe Gly Met Met Gly
        1060                1065                1070

Leu Ile Gly Ile Lys Leu Ser Ala Val Pro Val Ile Leu Ile Ala
    1075                1080                1085

Ser Val Gly Ile Gly Val Glu Phe Thr Val His Val Ala Leu Ala Phe
1090                1095                1100

Leu Thr Ala Ile Gly Asp Lys Asn Arg Arg Ala Val Leu Ala Leu Glu
1105                1110                1115                1120

His Met Phe Ala Pro Val Leu Asp Gly Ala Val Ser Thr Leu Leu Gly
            1125                1130                1135

Val Leu Met Leu Ala Gly Ser Glu Phe Asp Phe Ile Val Arg Tyr Phe
        1140                1145                1150

Phe Ala Val Leu Ala Ile Leu Thr Ile Leu Gly Val Leu Asn Gly Leu
    1155                1160                1165

Val Leu Leu Pro Val Leu Leu Ser Phe Phe Gly Pro Tyr Pro Glu Val
1170                1175                1180

Ser Pro Ala Asn Gly Leu Asn Arg Leu Pro Thr Pro Ser Pro Glu Pro
1185                1190                1195                1200

Pro Pro Ser Val Val Arg Phe Ala Met Pro Pro Gly His Thr His Ser
            1205                1210                1215

Gly Ser Asp Ser Ser Asp Ser Glu Tyr Ser Ser Gln Thr Thr Val Ser
        1220                1225                1230

Gly Leu Ser Glu Glu Leu Arg His Tyr Glu Ala Gln Gln Gly Ala Gly
    1235                1240                1245

Gly Pro Ala His Gln Val Ile Val Glu Ala Thr Glu Asn Pro Val Phe
1250                1255                1260

Ala His Ser Thr Val Val His Pro Glu Ser Arg His His Pro Pro Ser
1265                1270                1275                1280

Asn Pro Arg Gln Gln Pro His Leu Asp Ser Gly Ser Leu Pro Pro Gly
            1285                1290                1295

Arg Gln Gly Gln Gln Pro Arg Arg Asp Pro Pro Arg Glu Gly Leu Trp
        1300                1305                1310

Pro Pro Leu Tyr Arg Pro Arg Arg Asp Ala Phe Glu Ile Ser Thr Glu
    1315                1320                1325

Gly His Ser Gly Pro Ser Asn Arg Ala Arg Trp Gly Pro Arg Gly Ala
1330                1335                1340

Arg Ser His Asn Pro Arg Asn Pro Ala Ser Thr Ala Met Gly Ser Ser
1345                1350                1355                1360

Val Pro Gly Tyr Cys Gln Pro Ile Thr Thr Val Thr Ala Ser Ala Ser
            1365                1370                1375

Val Thr Val Ala Val His Pro Pro Val Pro Gly Pro Gly Arg Asn
        1380                1385                1390

Pro Arg Gly Gly Leu Cys Pro Gly Tyr Pro Glu Thr Asp His Gly Leu
    1395                1400                1405

Phe Glu Asp Pro His Val Pro Phe His Val Arg Cys Glu Arg Arg Asp
1410                1415                1420

Ser Lys Val Glu Val Ile Glu Leu Gln Asp Val Glu Cys Glu Glu Arg
1425                1430                1435                1440
```

Pro Arg Gly Ser Ser Ser Asn
                    1445

<210> SEQ ID NO 6
<211> LENGTH: 5605
<212> TYPE: DNA
<213> ORGANISM: Homo sapiens
<220> FEATURE:
<221> NAME/KEY: unsure
<222> LOCATION: (5021)
<221> NAME/KEY: unsure
<222> LOCATION: (5097)
<221> NAME/KEY: unsure
<222> LOCATION: (5166)
<221> NAME/KEY: unsure
<222> LOCATION: (5297)
<221> NAME/KEY: unsure
<222> LOCATION: (5391)

<400> SEQUENCE: 6

| | | | | | |
|---|---|---|---|---|---|
| actcgatctt | tttccccata | atggcctctc | tccttttgct | ttacagtgca | atcagggcag | 60 |
| aataacagat | atgttgagta | gctaatttat | atttctgaag | atctccatag | aactcttaag | 120 |
| ttctaagtct | tcatagtctt | tgcaccttgc | caagtttgct | ttcctttggg | aattctgtca | 180 |
| taaccacaag | ggttatcccc | agacatgcag | tttggggaaa | ttaacccggc | agtagtaaac | 240 |
| agactggatt | agaaaaggtg | gcagtcgtaa | taaggatatt | caataaccgg | ggaaagctac | 300 |
| agaaggatct | tgagttagga | tgatgacagt | tacaatagaa | aggagaccag | tacaagagac | 360 |
| ggtgaaaaca | gaatggatac | aatttagttg | aagaattggc | tgtgggtgaa | aagaagaaat | 420 |
| caaagatgcc | tgaagttgtg | agtttcaggt | agccctgagt | ttataatcct | agttctgact | 480 |
| cgtactatct | ttggatatac | tagctgctga | ctactaactg | aacaaggtag | taaccttgtc | 540 |
| atcttgtaac | ttacctaagt | ctgtttcctc | ctctataaaa | caaactatca | aaataaagcc | 600 |
| gatgaaaaga | ttgaagtaaa | acataaaacc | cttagcacag | tgcctagtat | ccattaagca | 660 |
| gtagataaat | gatggcggtc | attattaggg | agtagggtaa | agaacagaag | gttaaaaaca | 720 |
| tgagtagcag | taaggacttt | tgggtgggga | ttcggtcttt | ctactacaca | ttacacatac | 780 |
| ctctaagcag | agaaagggt | tggaggggag | tttgataatg | tgactaataa | tcctcctccc | 840 |
| cctgggggg | atcttgataa | aggatagcca | cccacatgga | ggcctaatat | aaactggatt | 900 |
| gcagaatgca | cttgagctgg | gagcccaagc | gggccaggct | tcttgattcc | tattttatcc | 960 |
| cctttaacct | aggatagcta | ggtctatagt | gcagactcag | acctaactta | cactttcatt | 1020 |
| tgcagctgaa | gtttcggaac | aaagacaaag | atagccagat | catattaatt | acacggatag | 1080 |
| gcaagaaagc | atgagccctg | aggaggaagg | aagggactgt | ccaggtgtac | ttacctcaaa | 1140 |
| gatgagaaat | atcaaagaca | ggaaaccta | ggttcttgcc | cttcagtcgc | tatctccttg | 1200 |
| ccattagtaa | aatgcggccg | atgaatgtcc | tcacttctgt | ccatctgggc | aggaggtggg | 1260 |
| aagggtgacg | tgcaaatgga | tgggaggaac | cctttttcg | gcagcaccca | ccacacccag | 1320 |
| cctagtgcca | cgcaccgcaa | gcgctccata | acgcacaca | gcgtcgcctc | taccaggatc | 1380 |
| ccgggcggcc | ttcgcgggat | ttctcctggc | gtcggctttc | agactcccga | gggtgggata | 1440 |
| aatcgagagg | gtggcatcct | ttggcttttc | ttctcccagg | cagctctgaa | ccatgtttat | 1500 |
| gcaacgttta | atgggctcta | ataaaacggc | taataatttt | gatccgcgga | agcaccgact | 1560 |
| cgctcgctaa | gccgaatctg | cgagggtgaa | gctgcaactc | caacgccgga | aagcgcggct | 1620 |
| accgaaaagc | gcatgcgcca | cggggtggca | cgaagctaga | gtaagctgag | gaggtgggcg | 1680 |
| gaaccatgg | caaccatggg | tgatgacgac | atggggagcg | tctctacgct | ggattatgac | 1740 |

```
gctggattat gacgcaggca gtgggcgcgg actctgcggt tcgcttgact gacggcgcag    1800
cctccgggcc tagccacagc agcaacggca gaggccagcg ggcgaggtca agatggtggc    1860
tccgcgggcg ggggaggcag tggagggagg aggagtcaga ccttagccag ccggaaacac    1920
cgaaacccag agacctcctg gggagccgcc gccgccgccc tctcggccat cgctgcctcc    1980
gccgcctgct ccacctcgag ggacgcgagc gggcggcggg gctggccgtg agagagacag    2040
gagaggaagg agggcagggg cggagttgcc cgccttagcc cccgccccg gccgcggccc     2100 cgggccctgc cccgcgcggc cctgcccggc ccaccgagcc ctggtgtggc agcggctcat    2160
ggcggccgtg gggcccccgc agcagcaggt gcggatggcc catcagcaga tctgggcggc    2220
gctcgaagtg gcgctccggg tgccctgcct ttacatcatc gacgccatct tcaactccta    2280
cccggattcc agccaaagcc ggttctgcat cgtgctccag atcttcctcc ggctctttgg    2340
taagggaaca gggtaccgta cgtcccggga cggctatgcg ggccgagacg ttccccgggg    2400
agcgggcagg cgcgcagagg ccatgggtcg agtatgtgtc tttgggaact acagtttcat    2460
ccctcaaagg gtcgtcttta cgggttggga ggggaagga gatgatactt gtctgagttg      2520
acagcggagc agtcccccta gcgaggattc agtgttgtac ctgagtgagg tggcgagaaa    2580
gtaaggatgt gtgagcatgc agctctttgc ccgtttgcct tgggaaatga gtactggctt    2640
accgcgtcct atgcgacagc cttcgaaaaa caactctgct atcccagtct cgtcgtgtgt    2700
gaccttggac ttctgccaag gcgtgggcct cagtttccct ttattaccaa atgccgagta    2760
cttgtatgtt gtcacttctg ctgcacccga gggtccacag gatcgtgaag tgtctgcagt    2820
aaatgacatc caagcgaagg agacagggtt ttgaatgtca gaccttgaaa ccattaccaa    2880
aaattctcat gaaagcggcg atgcttaaat cgagtcctaa aatttccat gaataaacga     2940 gaaggtattg aaagtgactg taaaaagtga tgagacattt gccaaagaga cttctgaaaa    3000
tcattgtctt tgtttcgtat ggatggagtg ttaaaagtat cttatatttc atttcttcct    3060
ttccatcttc acttacatca tcagagggag atgcatttat gcgtaaaata atttttaag    3120 taattgtaac ttggcaaatt tgttgatga ggtaattctg gtgatcggtc ttaagtaggc      3180
tagtgctttt gaagtgttgc tgagggcaga ctgatggtga ggtctttacc aagcctttct    3240
gaattacaag ccatctgttg ctttattcct tcaaagagg agtggcaata aaggccgaat      3300
tttgttctta gcaataaata gccatatttt acatttatct ggtattttcc ttttgcaaag    3360
cattttcact ggtaggtatt atctaaccta accttcaaac atcccccaga ggtgggtggt    3420
ggtattgtca ttttacaaac caggaaacag ggtcatagag gttaagtgtt ttgctcttgg    3480
taggctgccg ctaagtggtt gccagagcct gagcttaaaa atcttttgac attaaatatg    3540
gtttactttc ctccctaaca gctgcaatcc agatacagaa tgcagtagta atgatcatat    3600
gctagatctt aaaactaaag atgtaaacgt gatgttcagc ccaagctgct tcagtaaccc    3660
acctgctacc taattccagc ctttcctact tgccactgct aacgtatacc accaccataa    3720
tttgtgttaa aaactgggct ctgtttgaga ggattctgca tgttcatccc agaaacagtg    3780
tagtgactgc tttgaatatt cttacagcat gataactgca gattctgtga gaatcccttt    3840
gggacctggt gctttaatgc agtagtctgt tgagcttcag gttaggcagc ttcaaggaaa    3900
agaagtattt tctttaataa ataatttgta gtgtaagaac attgaacaaa gcaatctgat    3960
attttccttg tactaggcat gtttcttttg taataaatct tggaagtttg tgtttgacaa    4020
agaacaacat gacttaaggc aactgctcag tgctttggtt tcttatttt acctttaaa      4080
```

-continued

```
agatggagag tgaggttatc tgtttcatag ggtgttaaag acaataaatc tattttaatg      4140
cttcatttaa taccatattt tgttagatat tttggtcttt tgaaatcatc ggcaaaatat      4200
tggtgttgtt tatttgaaaa ttttgatccc tggaatctct ggatcagact ttgagaaata      4260
cgaaatactc ttcaaatcta tcatccgact cttcttactg tgtcatgtaa ttatgctaat      4320
ttttcacatt tgtaaggatg ataagaatga aaaaaactga tttcggtgct aaaaattatg      4380
ttactaaaag acacaggttt gtgtgtaaat atgccaatgg atagttgaaa ttaatcgttc      4440
tgccttgtta gttttttttgt agttgtagac ttctcagtac tactgtgtat aagtcttacc     4500
acttgtcaac ctcactttt tctttaaaat taatgtgtaa aaatggaaat ctctaagtaa       4560
aaagcattac cagttttatg tgtggtggta aagtattta ctccctcta cctacaaaat       4620 ggtgctacaa ctgtaccttc atttgatatc aaactaattt gagatttcaa ccggttagaa      4680
aataaagcaa ctcattttgg agatccaaat aaaattctat gacaatatat ggaatattga      4740
agaacataaa gctgtgtttt aagggatgtt aaatactaaa cgaaactcaa cccagagcag      4800
cataatgctg agttagcaaa tttaaatcca aggcagaaaa tgcaagccta ggagtttgtt      4860
ttaatagtat tactaatatg gtgataattc attgaggtgg gaaaaggctt taaacataac      4920
agaagaccca gaagttccaa ggaaaaatct gaaaaatttc agtacataaa aataaaaagc      4980 tttttatgg caaagcttaa aaaagaatcc ttaaatgaca nactgagata aaatacttct       5040
atcataagtg attcacgttc cagtaagagt tttaccctgc cagggaagct gaggcangag      5100
aatcgcttga accaaggagt tgcaggttgc agtgagccga gatcgctcca ctgcactcca      5160
gcctgnggat agagtgagac tctgtctaaa aaaaaaaaca aaacaaaaca agaaaaaact      5220
tatactccct taggaaaatg cctaagacaa gcaattcaca ataaacaaaa tgcagatgtt      5280
caataagcaa gagaaanagt atttagccct tcctgcagta gcttgatttt atgggggaaa      5340
aaaaaaagta ctagccttgt ttataattaa atactgtcaa gaccgcttac nggtgctcac      5400
gcctataatc ccagcacttt gggaggctga ggcaagcaga tttgcttatg ccaggagttg      5460
acaacagctt tggcaaatgg cacaacccgt gtcaacaaat aattaaccgg gtgcaatgac      5520
tcctggccat attccaacct acgggtttgg agctttcaca taatttcttt attcagggag      5580
gttttagtgc cattagcatt atagt                                            5605
```

<210> SEQ ID NO 7
<211> LENGTH: 2517
<212> TYPE: DNA
<213> ORGANISM: Homo sapiens
<220> FEATURE:
<221> NAME/KEY: repeat_unit
<222> LOCATION: (165)..(176)

<400> SEQUENCE: 7

```
gaaacccaga gacctcctgg ggagccgccg ccgccgccct ctcggccatc gctgcctccg       60
ccgcctgctc cacctcgagg gacgcgagcg ggcggcgggg ctggccgtga gagagacagg      120
agaggaagga gggcagggc ggagttgccc gccttagccc ccgccttagc ccccgccccc      180
ggccgcggcc ccgggccctg ccccgcgcgg ccctgcccgg ccaccgagc cctggtgtgg      240 cagcggctca tggcggccgt ggggcccccg cagcagcagg tgcggatggc ccatcagcag      300
atctgggcgg cgctcgaagt ggcgctccgg gtgccctgcc tttacatcat cgacgccatc      360
ttcaactcct acccggattc cagccaaagc cggttctgca tcgtgctcca gatcttcctc      420
cggctctttg gtgtatttgc atccagtatt gttctgatct tgtcacaacg atcactttc      480
```

-continued

```
aagttttaca cgtacagctc agcctttctg ttagctgcaa cttcagtgtt ggtgaattat      540
tatgcttctt tgcacattga cttctatggt gcctacaaca cgtcagcttt tggaattgag      600
ctgcttcctc gaaaaggtcc ctcgctgtgg atggcactta cgttctaca gctaacattt       660 ggaattggat acgttacact actccagatt cattccatct attcacaatt aattattttg      720
gatctcttgg ttcctgtaat aggcttaatc acagagctac cattacacat cagagagact     780
ttactgttta cttcttcctt gattctcaca ttaaatacag tgtttgtcct ggcagtgaaa      840
ctgaagtggt tttattattc cacacgatat gtttatcttt tggtgaggca catgtatcga      900
atttatggat tacagttatt gatggaggac acatggaaga ggattcgttt cccagacata      960
ctacgagtct tttggctaac aagagttaca gctcaggcta cagtgttaat gtacatctta    1020
aggatggcaa atgaaactga ttccttcttt atttcttggg atgattttg ggacctcatt     1080 tgcaatctta taattagtgg gtgcgattct acactaactg tactgggcat gagtgctgta    1140
atttcctcag tagcccatta tttggggctt ggaatattgg cctttattgg atcaactgag    1200
gaagatgaca ggcgtcttgg cttgttgca cctgttttat tttttatttt ggctcttcag     1260
actgggttaa gtgggctaag accagaagag agacttattc gcttaagtag aaacatgtgc    1320
cttttattaa ctgcagtcct gcattttatc catggaatga cagaccctgt attaatgtct    1380
ctcagtgcct ctcatgtgtc atcttttcgt agacattttc ctgtgctgtt tgtctctgct    1440
tgcctgttta ttcttcctgt cttactcagt tatgttcttt ggcatcacta tgcactaaat    1500
acatggttgt ttgcagttac agcattttgt gtggaactgt gcttaaaagt aattgtttct    1560
ctcactgttt atacgttatt catgattgat ggctactata atgtcctctg gaaaagctt     1620 gacgattatg tctactacgt tcgttcaaca ggcagtatta ttgaattat atttggagtt     1680 gtaatgtttg gaaatggggc ttacactatg atgtttgagt cgggaagtaa aattcgggct    1740
tttatgatgt gcctacatgc atattttaac atctacttac aagccaaaaa tggctggaag    1800
acatttatga atcgtaggac tgctgtgaag aaaattaatt cacttcctga aataaaaggg    1860
agccgcttac aagaaataaa tgatgtatgt gcaatctgct atcatgagtt tacaacatct    1920
gctcgtatta caccgtgtaa tcattatttc catgcacttt gccttcggaa atggctgtac    1980
attcaagata cttgtccaat gtgccatcag aaagtataca tcgaagatga tatcaaggat    2040
aattcaaatg tatctaacaa caatggattt attccaccca atgaaactcc agaggaagct    2100
gtaagagaag ctgctgctga atctgacagg gaattgaacg aagatgacag tacagattgt    2160
gatgatgatg ttcaaagaga aagaaatgga gtgattcagc acacaggcgc agcagctgaa    2220
gaatttaatg atgatactga ctgatgaaaa tagcatttat taatgattga ggtatttgtt    2280
taaaattcag ttcatccaaa atggagtaat atccttcacc ttcagtgtgt aaccaagcac    2340
aaaaacagta tcaatgttga atctgtgaat ggttttccgt ttactgtgat gtgctactgt    2400
aaatatacct ctttaattac ttctggtctc tttggtgacc tgtttaaatt tgtgtacatt    2460
attgtacata gaataaaatg ttttcacatt tttatgacaa aaaaaaaaa aaaaaaa        2517
```

<210> SEQ ID NO 8
<211> LENGTH: 1095
<212> TYPE: DNA
<213> ORGANISM: Homo sapiens
<220> FEATURE:
<221> NAME/KEY: CDS
<222> LOCATION: (363)..(806)

<400> SEQUENCE: 8

-continued

```
tcccgctct gctctgtccg gtcacaggac tttttgccct ctgttccgg gtccctcagg      60 cggccaccca gtgggcacac tcccaggcgg cgctccggcc ccgcgctccc tccctctgcc    120
tttcattccc agctgtcaac atcctggaag ctttgaagct caggaaagaa gagaaatcca    180
ctgagaacag tctgtaaagg tccgtagtgc tatctacatc cagacggtgg aagggagaga    240
aagagaaaga aggtatccta ggaatacctg cctgcttaga ccctctataa agctctgtg     300 catcctgcca ctgaggactc cgaagaggta gcagtcttct gaaagacttc aactgtgagg    360
```

```
ac atg tcg ttc aga ttt ggc caa cat ctc atc aag ccc tct gta gtg      407
   Met Ser Phe Arg Phe Gly Gln His Leu Ile Lys Pro Ser Val Val
    1               5                  10                  15 ttt ctc aaa aca gaa ctg tcc ttc gct ctt gtg aat agg aaa cct gtg     455
Phe Leu Lys Thr Glu Leu Ser Phe Ala Leu Val Asn Arg Lys Pro Val
            20                  25                  30 gta cca gga cat gtc ctt gtg tgc ccg ctg cgg cca gtg gag cgc ttc    503
Val Pro Gly His Val Leu Val Cys Pro Leu Arg Pro Val Glu Arg Phe
        35                  40                  45 cat gac ctg cgt cct gat gaa gtg gcc gat ttg ttt cag acg acc cag    551
His Asp Leu Arg Pro Asp Glu Val Ala Asp Leu Phe Gln Thr Thr Gln
    50                  55                  60 aga gtc ggg aca gtg gtg gaa aaa cat ttc cat ggg acc tct ctc acc    599
Arg Val Gly Thr Val Val Glu Lys His Phe His Gly Thr Ser Leu Thr
65                  70                  75 ttt tcc atg cag gat ggc ccc gaa gcc gga cag act gtg aag cac gtt    647
Phe Ser Met Gln Asp Gly Pro Glu Ala Gly Gln Thr Val Lys His Val
 80                  85                  90                  95 cac gtc cat gtt ctt ccc agg aag gct gga gac ttt cac agg aat gac    695
His Val His Val Leu Pro Arg Lys Ala Gly Asp Phe His Arg Asn Asp
            100                 105                 110 agc atc tat gag gag ctc cag aaa cat gac aag gag gac ttt cct gcc    743
Ser Ile Tyr Glu Glu Leu Gln Lys His Asp Lys Glu Asp Phe Pro Ala
        115                 120                 125 tct tgg aga tca gag gag gaa atg gca gca gaa gcc gca gct ctg cgg    791
Ser Trp Arg Ser Glu Glu Glu Met Ala Ala Glu Ala Ala Ala Leu Arg
    130                 135                 140 gtc tac ttt cag tga cacagatgtt tttcagatcc tgaattccag caaaagagct    846
Val Tyr Phe Gln
    145
```

```
attgccaacc agtttgaaga ccgccccccc gcctctcccc aagaggaact gaatcagcat    906
gaaaatgcag tttcttcatc tcaccatcct gtattcttca accagtgatc ccccacctcg    966
gtcactccaa ctcccttaaa atacctagac ctaaacggct cagacaggca gatttgaggt   1026 ttcccctgt ctccttattc ggcagcctta tgattaaact tccttctctg ctgcaaaaaa    1086
aaaaaaaaa                                                            1095
```

<210> SEQ ID NO 9
<211> LENGTH: 147
<212> TYPE: PRT
<213> ORGANISM: Homo sapiens

<400> SEQUENCE: 9

```
Met Ser Phe Arg Phe Gly Gln His Leu Ile Lys Pro Ser Val Val Phe
 1               5                  10                  15

Leu Lys Thr Glu Leu Ser Phe Ala Leu Val Asn Arg Lys Pro Val Val
            20                  25                  30

Pro Gly His Val Leu Val Cys Pro Leu Arg Pro Val Glu Arg Phe His
        35                  40                  45
```

```
Asp Leu Arg Pro Asp Glu Val Ala Asp Leu Phe Gln Thr Thr Gln Arg
         50                  55                  60

Val Gly Thr Val Val Glu Lys His Phe His Gly Thr Ser Leu Thr Phe
 65                  70                  75                  80

Ser Met Gln Asp Gly Pro Glu Ala Gly Gln Thr Val Lys His Val His
                 85                  90                  95

Val His Val Leu Pro Arg Lys Ala Gly Asp Phe His Arg Asn Asp Ser
                100                 105                 110

Ile Tyr Glu Glu Leu Gln Lys His Asp Lys Glu Asp Phe Pro Ala Ser
            115                 120                 125

Trp Arg Ser Glu Glu Glu Met Ala Ala Glu Ala Ala Ala Leu Arg Val
        130                 135                 140

Tyr Phe Gln
145

<210> SEQ ID NO 10
<211> LENGTH: 1261
<212> TYPE: DNA
<213> ORGANISM: Homo sapiens

<400> SEQUENCE: 10
gaaacccaga gacctcctgg ggagccgccg ccgccgccct ctcggccatc gctgcctccg      60
ccgcctgctc cacctcgagg gacgcgagcg ggcggcgggg ctggccgtga gagagacagg     120
agaggaagga gggcaggggc ggagttgccc gccttagccc ccgcccccgg ccgcggcccc     180
gggccctgcc ccgcgcggcc ctgcccggcc caccgagccc tggtgtggca gcggctcatg     240
gcggccgtgg ggcccccgca gcagcaggtg cggatggccc atcagcagat ctgggcggcg     300
ctcgaagtgg cgctccgggt gccctgcctt acatcatcg acgccatctt caactcctac      360
ccggattcca gccaaagccg gttctgcatc gtgctccaga tcttcctccg gctctttggt     420
atcctaggaa tacctgcctg cttagaccct ctataaaagc tctgtgcatc ctgccactga     480
ggactccgaa gaggtagcag tcttctgaaa gacttcaact gtgaggacat gtcgttcaga     540
tttggccaac atctcatcaa gccctctgta gtgtttctca aaacagaact gtccttcgct     600
cttgtgaata ggaaacctgt ggtaccagga catgtccttg tgtgcccgct gcggccagtg     660
gagcgcttcc atgacctgcg tcctgatgaa gtggccgatt tgtttcagac gacccagaga     720
gtcgggacag tggtgaaaaa acatttccat gggacctctc tcacctttc catgcaggat      780 ggccccgaag ccggacagac tgtgaagcac gttcacgtcc atgttcttcc caggaaggct     840
ggagactttc acaggaatga cagcatctat gaggagctcc agaaacatga caaggaggac     900
tttcctgcct cttggagatc agaggaggaa atggcagcag aagccgcagc tctgcgggtc     960
tactttcagt gacacagatg tttttcagat cctgaattcc agcaaagag ctattgccaa     1020 ccagtttgaa gaccgccccc ccgcctctcc ccaagaggaa ctgaatcagc atgaaaatgc    1080
agtttcttca tctcaccatc ctgtattctt caaccagtga tcccccacct cggtcactcc    1140 aactcccttta aaatacctag acctaaacgg ctcagacagg cagatttgag gtttccccct   1200
gtctccttat tcggcagcct tatgattaaa cttccttctc tgctgcaaaa aaaaaaaaa    1260 a                                                                    1261

<210> SEQ ID NO 11
<211> LENGTH: 2339
<212> TYPE: DNA
<213> ORGANISM: Homo sapiens
```

<400> SEQUENCE: 11

```
tccccgctct gctctgtccg gtcacaggac tttttgccct ctgttccggg gtccctcagg      60
cggccaccca gtgggcacac tcccaggcgg cgctccggcc ccgcgctccc tccctctgcc     120
tttcattccc agctgtcaac atcctggaag ctttgaagct caggaaagaa gagaaatcca     180
ctgagaacag tctgtaaagg tccgtagtgc tatctcatc cagacggtgg aagggagaga      240
aagagaaaga aggtgtattt gcatccagta ttgttctgat cttgtcacaa cgatcacttt     300
tcaagtttta cacgtacagc tcagcctttc tgttagctgc aacttcagtg ttggtgaatt     360
attatgcttc tttgcacatt gacttctatg gtgcctacaa cacgtcagct tttggaattg     420
agctgcttcc tcgaaaaggt ccctcgctgt ggatggcact tatcgttcta cagctaacat     480
ttggaattgg atacgttaca ctactccaga ttcattccat ctattcacaa ttaattattt     540
tggatctctt ggttcctgta ataggcttaa tcacagagct accattacac atcagagaga     600
ctttactgtt tacttcttcc ttgattctca cattaaatac agtgtttgtc ctggcagtga     660
aactgaagtg gtttttattat tccacacgat atgtttatct tttggtgagg cacatgtatc    720
gaatttatgg attacagtta ttgatggagg acacatggaa gaggattcgt ttcccagaca     780
tactacgagt cttttggcta acaagagtta cagctcaggc tacagtgtta atgtacatct     840
taaggatggc aaatgaaact gattccttct ttatttcttg ggatgatttt tgggacctca     900
tttgcaatct tataattagt gggtgcgatt ctacactaac tgtactgggc atgagtgctg     960
taatttcctc agtagcccat tatttgggc ttggaatatt ggcctttatt ggatcaactg     1020
aggaagatga caggcgtctt ggctttgttg cacctgtttt attttttatt ttggctcttc    1080
agactgggtt aagtgggcta agaccagaag agagacttat tcgcttaagt agaaacatgt    1140
gcctttatt aactgcagtc ctgcatttta tccatggaat gacagaccct gtattaatgt     1200
ctctcagtgc ctctcatgtg tcatctttc gtagacattt tcctgtgctg tttgtctctg     1260
cttgcctgtt tattcttcct gtcttactca gttatgttct ttggcatcac tatgcactaa    1320
atacatggtt gtttgcagtt acagcatttt gtgtggaact gtgcttaaaa gtaattgttt    1380
ctctcactgt ttatacgtta ttcatgattg atggctacta taatgtcctc tgggaaaagc    1440
ttgacgatta tgtctactac gttcgttcaa caggcagtat tattgaattt atatttggag    1500
ttgtaatgtt tggaaatggg gcttacacta tgatgtttga gtcgggaagt aaaattcggg    1560
cttttatgat gtgcctacat gcatatttta acatctactt acaagccaaa aatggctgga    1620
agacatttat gaatcgtagg actgctgtga agaaaattaa ttcacttcct gaaataaaag    1680
ggagccgctt acaagaaata aatgatgtat gtgcaatctg ctatcatgag tttacaacat    1740
ctgctcgtat tacaccgtgt aatcattatt tccatgcact ttgccttcgg aaatggctgt    1800
acattcaaga tacttgtcca atgtgccatc agaaagtata catcgaagat gatatcaagg    1860
ataattcaaa tgtatctaac aacaatggat ttattccacc caatgaaact ccagaggaag    1920
ctgtaagaga agctgctgct gaatctgaca gggaattgaa cgaagatgac agtacagatt    1980
gtgatgatga tgttcaaaga gaaagaaatg gagtgattca gcacacaggc gcagcagctg    2040
aagaatttaa tgatgatact gactgatgaa aatagcattt attaatgatt gaggtatttg    2100
tttaaaattc agttcatcca aaatggagta atatccttca ccttcagtgt gtaaccaagc    2160
acaaaaacag tatcaatgtt gaatctgtga atggttttcc gtttactgtg atgtgctact    2220
gtaaatatac ctcttaatt acttctggtc tctttggtga cctgttaaa tttgtgtaca     2280
ttattgtaca tagaataaaa tgttttcaca tttttatgac aaaaaaaaaa aaaaaaaa      2339
```

<210> SEQ ID NO 12
<211> LENGTH: 22
<212> TYPE: DNA
<213> ORGANISM: Homo sapiens

<400> SEQUENCE: 12
tcagaagact gctacctctt cg                                    22

<210> SEQ ID NO 13
<211> LENGTH: 19
<212> TYPE: DNA
<213> ORGANISM: Homo sapiens

<400> SEQUENCE: 13
tcagtggcag gatgcacag                                        19

<210> SEQ ID NO 15
<211> LENGTH: 21
<212> TYPE: DNA
<213> ORGANISM: Homo sapiens

<400> SEQUENCE: 15
ggtctaagca ggcaggtatt c                                     21

<210> SEQ ID NO 16
<211> LENGTH: 18
<212> TYPE: DNA
<213> ORGANISM: Homo sapiens

<400> SEQUENCE: 16
tggaagggag agaaagag                                         18

<210> SEQ ID NO 17
<211> LENGTH: 16
<212> TYPE: DNA
<213> ORGANISM: Homo sapiens

<400> SEQUENCE: 17
ggtattccta ggatac                                           16

<210> SEQ ID NO 18
<211> LENGTH: 19
<212> TYPE: DNA
<213> ORGANISM: Homo sapiens

<400> SEQUENCE: 18
tccctctgcc tttcattcc                                        19

<210> SEQ ID NO 19
<211> LENGTH: 22
<212> TYPE: DNA
<213> ORGANISM: Homo sapiens

<400> SEQUENCE: 19
gccctgcctt tacatcatcg ac                                    22

<210> SEQ ID NO 20
<211> LENGTH: 23
<212> TYPE: DNA
<213> ORGANISM: Homo sapiens

<400> SEQUENCE: 20

-continued agatctggag cacgatgcag aac    23

<210> SEQ ID NO 21
<211> LENGTH: 21
<212> TYPE: DNA
<213> ORGANISM: Homo sapiens

<400> SEQUENCE: 21
tcttgttagc caaaagactc g    21

<210> SEQ ID NO 22
<211> LENGTH: 17
<212> TYPE: DNA
<213> ORGANISM: Homo sapiens

<400> SEQUENCE: 22
agttgcccgc cttagcc    17

<210> SEQ ID NO 23
<211> LENGTH: 21
<212> TYPE: DNA
<213> ORGANISM: Homo sapiens

<400> SEQUENCE: 23
ccaaagacac atactcgacc c    21

<210> SEQ ID NO 24
<211> LENGTH: 25
<212> TYPE: DNA
<213> ORGANISM: Homo sapiens

<400> SEQUENCE: 24
cataactctt agtggggaaa cattc    25

<210> SEQ ID NO 25
<211> LENGTH: 23
<212> TYPE: DNA
<213> ORGANISM: Homo sapiens

<400> SEQUENCE: 25
tgtaacgtat ccaattccaa atg    23

<210> SEQ ID NO 26
<211> LENGTH: 21
<212> TYPE: DNA
<213> ORGANISM: Homo sapiens

<400> SEQUENCE: 26
tggcacttat cgttctacag c    21

<210> SEQ ID NO 27
<211> LENGTH: 21
<212> TYPE: DNA
<213> ORGANISM: Homo sapiens

<400> SEQUENCE: 27
tcttgttagc caaaagactc g    21

<210> SEQ ID NO 28
<211> LENGTH: 19
<212> TYPE: DNA
<213> ORGANISM: Homo sapiens

<400> SEQUENCE: 28

-continued agtgtttgtc ctggcagtg          19

<210> SEQ ID NO 29
<211> LENGTH: 23
<212> TYPE: DNA
<213> ORGANISM: Homo sapiens

<400> SEQUENCE: 29
acagttagtg tagaatcgca ccc          23

<210> SEQ ID NO 30
<211> LENGTH: 20
<212> TYPE: DNA
<213> ORGANISM: Homo sapiens

<400> SEQUENCE: 30
tggcaaatga aactgattcc          20

<210> SEQ ID NO 31
<211> LENGTH: 21
<212> TYPE: DNA
<213> ORGANISM: Homo sapiens

<400> SEQUENCE: 31
catggataaa atgcaggact g          21

<210> SEQ ID NO 32
<211> LENGTH: 24
<212> TYPE: DNA
<213> ORGANISM: Homo sapiens

<400> SEQUENCE: 32
aagaccagaa gagagactta ttcg          24

<210> SEQ ID NO 33
<211> LENGTH: 20
<212> TYPE: DNA
<213> ORGANISM: Homo sapiens

<400> SEQUENCE: 33
tgctgtaact gcaaacaacc          20

<210> SEQ ID NO 34
<211> LENGTH: 20
<212> TYPE: DNA
<213> ORGANISM: Homo sapiens

<400> SEQUENCE: 34
tctttggcat cactatgcac          20

<210> SEQ ID NO 35
<211> LENGTH: 22
<212> TYPE: DNA
<213> ORGANISM: Homo sapiens

<400> SEQUENCE: 35
cttcacagca gtcctacgat tc          22

<210> SEQ ID NO 36
<211> LENGTH: 19
<212> TYPE: DNA
<213> ORGANISM: Homo sapiens
<210> SEQ ID NO 36
<211> LENGTH: 19
<212> TYPE: DNA
<213> ORGANISM: Homo sapiens

<400> SEQUENCE: 36
ccaaaaatgg ctggaagac                                                    19

<210> SEQ ID NO 37
<211> LENGTH: 19
<212> TYPE: DNA
<213> ORGANISM: Homo sapiens

<400> SEQUENCE: 37
tgtcagattc agcagcagc                                                    19

<210> SEQ ID NO 38
<211> LENGTH: 19
<212> TYPE: DNA
<213> ORGANISM: Homo sapiens

<400> SEQUENCE: 38
ccacccaatg aaactccag                                                    19

<210> SEQ ID NO 39
<211> LENGTH: 22
<212> TYPE: DNA
<213> ORGANISM: Homo sapiens

<400> SEQUENCE: 39
agtagcacat cacagtaaac gg                                                22

<210> SEQ ID NO 40
<211> LENGTH: 18
<212> TYPE: DNA
<213> ORGANISM: Homo sapiens

<400> SEQUENCE: 40
tcccaggcag ctctgaac                                                     18

<210> SEQ ID NO 41
<211> LENGTH: 18
<212> TYPE: DNA
<213> ORGANISM: Homo sapiens

<400> SEQUENCE: 41
accatcttga cctcgccc                                                     18

<210> SEQ ID NO 42
<211> LENGTH: 18
<212> TYPE: DNA
<213> ORGANISM: Homo sapiens

<400> SEQUENCE: 42
gttcgcttga ctgacggc                                                     18

<210> SEQ ID NO 43
<211> LENGTH: 17
<212> TYPE: DNA
<213> ORGANISM: Homo sapiens

<400> SEQUENCE: 43
atgagccgct gccacac                                                      17

<210> SEQ ID NO 44
<211> LENGTH: 18
<212> TYPE: DNA

```
<213> ORGANISM: Homo sapiens

<400> SEQUENCE: 44
caccgaaacc cagagacc                                              18

<210> SEQ ID NO 45
<211> LENGTH: 21
<212> TYPE: DNA
<213> ORGANISM: Homo sapiens

<400> SEQUENCE: 45
ccaaagacac atactcgacc c                                          21

<210> SEQ ID NO 46
<211> LENGTH: 61
<212> TYPE: PRT
<213> ORGANISM: Artificial Sequence
<220> FEATURE:
<223> OTHER INFORMATION: Description of Artificial Sequence:Ring-finger
      motif of the RING-H2 subtype
<221> NAME/KEY: UNSURE
<222> LOCATION: (2)..(3)
<223> OTHER INFORMATION: Must be exactly two Xaa at this location; Xaa
      can be any amino acid
<221> NAME/KEY: UNSURE
<222> LOCATION: (5)..(31)
<223> OTHER INFORMATION: Must be at least 9 Xaa residues in this region
      and as many as 27 xaa residues, where Xaa is any amino acid.
<221> NAME/KEY: UNSURE
<222> LOCATION: (33)
<221> NAME/KEY: UNSURE
<222> LOCATION: (35)..(36)
<223> OTHER INFORMATION: Must be exactly 2 Xaa at this location; Xaa can
      be any amino acid.
<221> NAME/KEY: UNSURE
<222> LOCATION: (38)..(39)
<223> OTHER INFORMATION: Must be exactly 2 Xaa at this location; Xaa can
      be any amino acid.
<221> NAME/KEY: UNSURE
<222> LOCATION: (41)..(57)
<223> OTHER INFORMATION: At least 6 Xaa must be present in this region
      up to a maximum of 17 Xaa.  Xaa can be any amino acid.
<221> NAME/KEY: UNSURE
<222> LOCATION: (59)..(60)
<223> OTHER INFORMATION: Must be exactly 2 Xaa at this positon; Xaa can
      be any amino acid.

<400> SEQUENCE: 46

Cys Xaa Xaa Cys Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Cys
             20                  25                  30

Xaa His Xaa Xaa His Xaa Xaa Cys Xaa Xaa Xaa Xaa Xaa Xaa Xaa
         35                  40                  45

Xaa Xaa Xaa Xaa Xaa Xaa Xaa Xaa Xaa Cys Xaa Xaa Cys
     50                  55                  60
```